United States Patent
Callister et al.

(10) Patent No.: US 10,983,121 B2
(45) Date of Patent: Apr. 20, 2021

(54) COMPOSITIONS AND METHODS FOR DIAGNOSING LYME DISEASE AND FOR PREDICTING LYME DISEASE SPIROCHETE ELIMINATION AFTER TREATMENT

(71) Applicants: QIAGEN Sciences LLC, Germantown, MD (US); Biopeptides Corp., East Setauket, NY (US); Gundersen Lutheran Medical Foundation, Inc., La Crosse, WI (US)

(72) Inventors: Steven M. Callister, Onalaska, WI (US); Jeff Boyle, Germantown, MD (US); Misato Miyamasu, Silver Spring, MD (US); Raymond Dattwyler, East Setauket, NY (US); Paul M. Arnaboldi, Patterson, NY (US)

(73) Assignees: QIAGEN Sciences LLC, Germantown, MD (US); Biopeptides Corp., East Setauket, NY (US); Gundersen Lutheran Medical Foundation, Inc., La Crosse, WI (US)

( * ) Notice: Subject to any disclaimer, the term of this patent is extended or adjusted under 35 U.S.C. 154(b) by 0 days.

(21) Appl. No.: 15/763,032

(22) PCT Filed: Sep. 15, 2016

(86) PCT No.: PCT/US2016/051896
§ 371 (c)(1),
(2) Date: Mar. 23, 2018

(87) PCT Pub. No.: WO2017/053167
PCT Pub. Date: Mar. 30, 2017

(65) Prior Publication Data
US 2019/0285630 A1 Sep. 19, 2019

Related U.S. Application Data

(60) Provisional application No. 62/233,192, filed on Sep. 25, 2015.

(51) Int. Cl.
*G01N 33/569* (2006.01)
*C07K 14/20* (2006.01)

(52) U.S. Cl.
CPC .......... *G01N 33/569* (2013.01); *C07K 14/20* (2013.01); *G01N 2333/20* (2013.01); *G01N 2800/52* (2013.01); *Y02A 50/30* (2018.01)

(58) Field of Classification Search
CPC ............. G01N 33/569; G01N 2333/20; G01N 2800/52; Y02A 50/57; C07K 14/20
See application file for complete search history.

(56) References Cited

U.S. PATENT DOCUMENTS

| | | | | |
|---|---|---|---|---|
| 6,204,018 | B1 * | 3/2001 | Bergstom et al. ..... | C07K 14/20 435/69.3 |
| 6,214,355 | B1 * | 4/2001 | Hook et al. ............ | C07K 14/20 424/234.1 |

(Continued)

FOREIGN PATENT DOCUMENTS

| | | | | |
|---|---|---|---|---|
| EP | 2809348 | A2 * | 12/2014 | ....... G01N 33/56911 |
| JP | 8-506730 | A | 7/1996 | |

(Continued)

OTHER PUBLICATIONS

Aberer, "*Lyme borreliosis*—an update," *J. Dtsch. Dermatol. Ges.* 5(5):406-414, 2007. (10 pages).

(Continued)

*Primary Examiner* — Jana A Hines
(74) *Attorney, Agent, or Firm* — Seed IP Law Group LLP

(57) ABSTRACT

Compositions and methods are provided for detection, diagnosis and prognosis of Lyme disease (LD), including a method for confirming *Borrelia* spp. infection by contacting, in vitro, whole blood samples from subjects suspected of having LD with synthetic peptides comprising T-cell epitope-containing regions derived from *Borrelia* proteins that are expressed at different stages of Lyme disease, and (Continued)

indirectly detecting LD-specific activated T-cells by determining production of a T-cell immune response indicator (e.g., interferon-Y) in response to stimulation by the peptides. Also disclosed are methods for predicting elimination of LD spirochetes in LD patients who have undergone LD treatment, by exposing whole blood samples from such subjects to peptides comprising specific T-cell epitope regions of Borrelia proteins that are expressed at different stages of Lyme disease, and confirming a lack of Borrelia-specific activated T-cells in the samples by the absence of a detectable T-cell immune response indicator (e.g., interferon-Y).

18 Claims, 1 Drawing Sheet

Specification includes a Sequence Listing.

(56) References Cited

U.S. PATENT DOCUMENTS

| | | | |
|---|---|---|---|
| 7,008,625 | B2* | 3/2006 | Dattwyler et al. ........................ C07K 16/1207 424/192.1 |
| 2012/0142023 | A1 | 6/2012 | Ascoli et al. |
| 2015/0017666 | A1 | 1/2015 | Dattwyler et al. |

FOREIGN PATENT DOCUMENTS

| | | |
|---|---|---|
| JP | 2000-503842 A | 4/2000 |
| JP | 2001-516458 A | 9/2001 |
| JP | 2010-503384 A | 2/2010 |
| JP | 2011-518338 A | 6/2011 |
| JP | 2013-539032 A | 10/2013 |
| RU | 133313 U1 | 10/2013 |
| WO | 94/19488 A1 | 9/1994 |
| WO | 97/27301 A1 | 7/1997 |
| WO | 99/35272 A1 | 7/1999 |
| WO | 2008/031133 A2 | 3/2008 |
| WO | 2009/131665 A1 | 10/2009 |
| WO | 2012/039614 A1 | 3/2012 |
| WO | 2012/047607 A2 | 4/2012 |
| WO | 2013/116668 A2 | 8/2013 |
| WO | 2017/139715 A1 | 8/2017 |

OTHER PUBLICATIONS

Belknap et al., "Interferon-Gamma Release Assays," *Clin Lab Med.* 34:337-349, 2014.
Dattwyler et al., "Dissociation of Specific T- and B-Lymphocyte Responses to *Borrelia burgdorferi*," *The New England Journal of Medicine* 319(22):1441-1446, 1988. (7 pages).
Dattwyler, "A Commentary on the Treatment of Early Lyme Disease," *Clinical Infectious Diseases* 50:521-522, 2010.
Drecktrah et al., "An Inverted Repeat in the ospC Operator Is Required for Induction in *Borrelia burgdorferi*," *PLOS One* 8(7):e68799, 2013. (7 pages).
Ekerfelt et al., "Asymptomatic *Borrelia*-Seropositive individuals display the same incidence of *Borrelia*-specific interferon-gamma (IFN-γ)-secreting cells in blood as patients with clinical *Borrelia* infection," *Clin Exp Immunol.* 115(3):498-502, 1999.
Ferguson et al., "The Diagnostic Accuracy of Tests for Latent Tuberculosis Infection in Hemodialysis Patients: A Systematic Review and Meta-Analysis," *Transplantation* 99(5):1084-1091, 2015.
GenBank, "decorin binding protein B, partial [Borreliella burgdorferi]," Accession No. AAC70029.1, Nov. 4, 1998, 1 page.

GenBank, "flagellin, partial [Borreliella burgdorferi]," Accession No. ACI49679.1, Mar. 5, 2009, 1 page.
GenBank, "outer surface protein C, partial [Borreliella burgdorfer]," Accession No. ABQ42983.1, Apr. 6, 2015, 1 page.
GenBank, "integral outer membrane protein P66 [Borreliella burgdorferi B31]," Accession No. AAC66949.1, Jul. 30, 2018, 2 pages.
Glickstein et al., "Inflammatory Cytokine Production Predominates in Early Lyme Disease in Patients with Erythema Migrans," *Infection and Immunity* 71(10):6051-6053, 2003.
Jin et al., "An Enhanced ELISPOT Assay for Sensitive Detection of Antigen-Specific T Cell Responses to *Borrelia burgdorferi*," *Cells* 2(3):607-620, 2013.
Jin et al., "iSpot Lyme™: A New Generation of Lyme Disease Testing," *NeuroScience, Inc.* Apr. 2013. (3 pages).
Jobe et al., "Significantly Improved Accuracy of Diagnosis of Early Lyme Disease by Peptide Enzyme-Linked Immunosorbent Assay Based on the Borreliacidal Antibody Epitope of *Borrelia burgdorferi* OspC," *Clin. Vaccine Immunol.* 15(6):981-985, 2008.
Johnson et al., "Serodiagnosis of Lyme Disease: Accuracy of a Two-Step Approach Using a Flagella-Based ELISA and Immunoblotting," *The Journal of Infectious Diseases* 174:346-353, 1996.
Kowalski et al., "Antibiotic Treatment Duration and Long-Term Outcomes of Patients with Early Lyme Disease from a Lyme Disease-Hyperendemic Area," *Clinical Infectious Diseases* 50:512-520, 2010.
Liang et al., "*Borrelia burgdorferi* Changes Its Surface Antigenic Expression in Response to Host Immune Responses," *Infect. Immun.* 72(10):5759-5767, 2004.
Marc et al., "Novel Laboratory Assessments for the Detection of *Borrelia burgdorferi*," NeuroScience, Inc. Jun. 2010. (4 pages).
Mogilyansky et al., "Comparison of Western Immunoblotting and the C6 Lyme Antibody Test for Laboratory Detection of Lyme Disease," *Clinical and Diagnostic Laboratory Immunology* 11(5):924-929, 2004.
Pai et al., "Interferon-γ assays in the immunodiagnosis of tuberculosis: a systematic review," *The Lancet Infectious Diseases* 4(12):761-776, 2004.
Ruan et al., "Screening of latent tuberculosis infection by interferon-γ release assays in rheumatic patients: a systematic review and meta-analysis," *Clin Rheumatol* 35:417-425, 2016.
Salo et al., "Decorin binding by DbpA and B of *Borrelia garinii, Borrelia afzelii,* and *Borrelia burgdorferi* Sensu Stricto," *The Journal of Infectious Diseases* 204:65-73, 2011.
Schmit et al., "Analysis of *Borrelia burgdorferi* surface proteins as determinants in establishing host cell interactions," *Frontiers in Microbiology* 2(141), 2011. (8 pages).
Schutzer et al., "Whole-Genome Sequences of *Borrelia bissettii, Borrelia valaisiana,* and *Borrelia spielmani*," *Journal of Bacteriology* 194(2):545-546, 2011.
Shapiro, "Lyme Disease," *N. Engl J Med* 370(18): 1724-1731, 2014.
Sikand et al., "Diagnosis of Lyme Borreliosis by a Whole-Blood Gamma Interferon Assay for Cell-Mediated Immune Responses," *Clinical and Diagnostic Laboratory Immunology* 6(3):445, 1999.
Wright et al., "Diagnosis and Management of Lyme Disease," *American Family Physician* 85(11):1086-1093, 2012.
Yun et al., "Significant Reduction in Rate of Indeterminate Results of the QuantiFERON-TB Gold In-Tube Test by Shortening Incubation Delay," *Journal of Clinical Microbiology* 52(1):90-94, 2014.
Fallon et al., "Inflammation and central nervous system Lyme disease," Neurobiol. Dis. (2009), doi: 10.1016/j.nbd.2009.11.016, 8 pages.
Knigge et al., The outer surface lipoprotein OspA of *Borrelia burgdorferi* provides co-stimulatory signals to normal human peripheral $CD4^+$ and $CD8^+$ T lymphocytes, *Eur. J. Immunol.* 26:2299-2303, 1996.
Nayak et al., "Microfluidics-based point-of-care test for serodiagnosis of Lyme Disease," *Scientific Reports* 6:35069, p. 1-9, 2016.

* cited by examiner

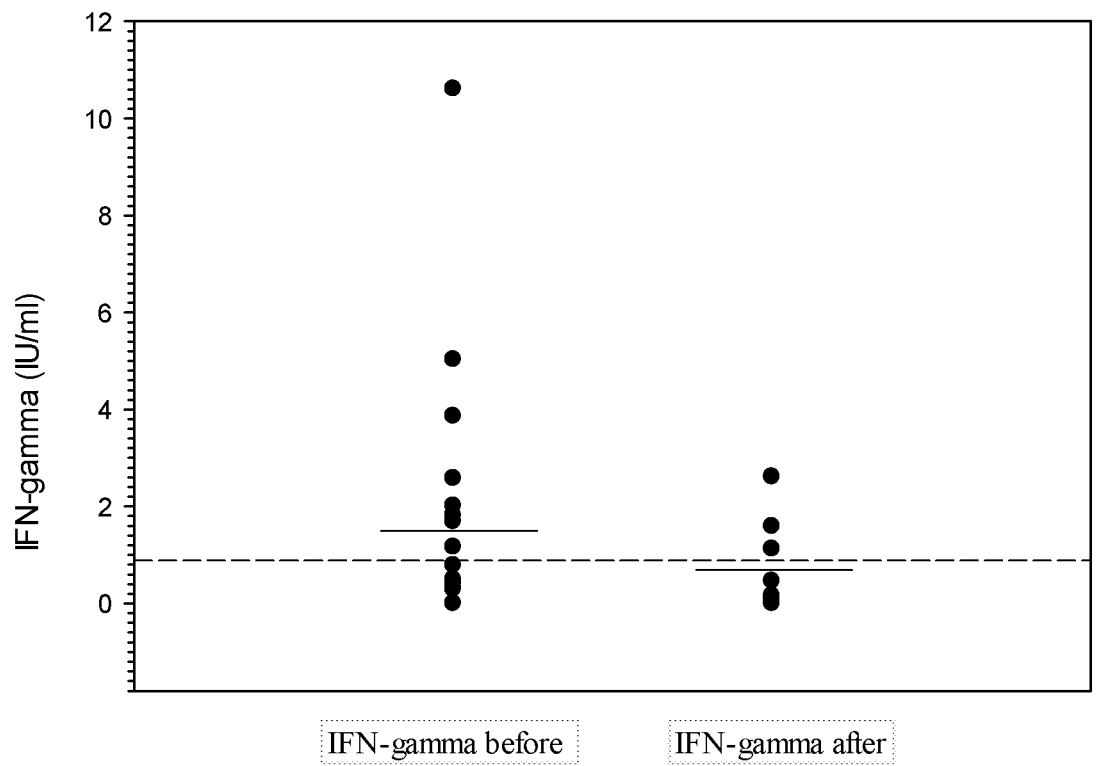

SEQUENCE LISTING

<160> NUMBER OF SEQ ID NOS: 40

<210> SEQ ID NO 1

-continued

```
<211> LENGTH: 25
<212> TYPE: PRT
<213> ORGANISM: Borrelia sp.

<400> SEQUENCE: 1

Asn Val Arg Thr Ala Glu Glu Leu Gly Met Gln Pro Ala Lys Ile Asn
1               5                   10                  15

Thr Pro Ala Ser Leu Ser Gly Ser Gln
            20                  25

<210> SEQ ID NO 2
<211> LENGTH: 20
<212> TYPE: PRT
<213> ORGANISM: Borrelia sp.

<400> SEQUENCE: 2

Asn Thr Pro Ala Ser Leu Ser Gly Ser Gln Ala Ser Trp Thr Leu Arg
1               5                   10                  15

Val His Val Gly
            20

<210> SEQ ID NO 3
<211> LENGTH: 20
<212> TYPE: PRT
<213> ORGANISM: Borrelia sp.

<400> SEQUENCE: 3

Leu Ser Gly Ser Gln Ala Ser Trp Thr Leu Arg Val His Val Gly Ala
1               5                   10                  15

Asn Gln Asp Glu
            20

<210> SEQ ID NO 4
<211> LENGTH: 20
<212> TYPE: PRT
<213> ORGANISM: Borrelia sp.

<400> SEQUENCE: 4

Gln Asp Glu Ala Ile Ala Val Asn Ile Tyr Ala Ala Asn Val Ala Asn
1               5                   10                  15

Leu Phe Ser Gly
            20

<210> SEQ ID NO 5
<211> LENGTH: 19
<212> TYPE: PRT
<213> ORGANISM: Borrelia sp.

<400> SEQUENCE: 5

Ser Leu Ala Lys Ile Glu Asn Ala Ile Arg Met Ile Ser Asp Gln Arg
1               5                   10                  15

Ala Asn Leu

<210> SEQ ID NO 6
<211> LENGTH: 20
<212> TYPE: PRT
<213> ORGANISM: Borrelia sp.

<400> SEQUENCE: 6

Ser Ile Val Met Val Leu Phe Phe Asp Leu Leu Val Ala Cys Ser Ile
1               5                   10                  15

Gly Leu Val Glu
```

```
                              20

<210> SEQ ID NO 7
<211> LENGTH: 20
<212> TYPE: PRT
<213> ORGANISM: Borrelia sp.

<400> SEQUENCE: 7

Leu Phe Phe Asp Leu Leu Val Ala Cys Ser Ile Gly Leu Val Glu Arg
1               5                   10                  15

Thr Asn Ala Ala
            20

<210> SEQ ID NO 8
<211> LENGTH: 25
<212> TYPE: PRT
<213> ORGANISM: Borrelia sp.

<400> SEQUENCE: 8

Ile Gly Leu Val Glu Arg Thr Asn Ala Ala Leu Glu Ser Ser Ser Lys
1               5                   10                  15

Asp Leu Lys Asn Lys Ile Leu Lys Ile
            20                  25

<210> SEQ ID NO 9
<211> LENGTH: 25
<212> TYPE: PRT
<213> ORGANISM: Borrelia sp.

<400> SEQUENCE: 9

Lys Asp Leu Lys Asn Lys Ile Leu Lys Ile Lys Lys Glu Ala Thr Gly
1               5                   10                  15

Lys Gly Val Leu Phe Glu Ala Phe Thr
            20                  25

<210> SEQ ID NO 10
<211> LENGTH: 25
<212> TYPE: PRT
<213> ORGANISM: Borrelia sp.

<400> SEQUENCE: 10

Gly Lys Gly Val Leu Phe Glu Ala Phe Thr Gly Leu Lys Thr Gly Ser
1               5                   10                  15

Lys Val Thr Ser Gly Gly Leu Ala Leu
            20                  25

<210> SEQ ID NO 11
<211> LENGTH: 25
<212> TYPE: PRT
<213> ORGANISM: Borrelia sp.

<400> SEQUENCE: 11

Ser Lys Val Thr Ser Gly Gly Leu Ala Leu Arg Glu Ala Lys Val Gln
1               5                   10                  15

Ala Ile Val Glu Thr Gly Lys Phe Leu
            20                  25

<210> SEQ ID NO 12
<211> LENGTH: 25
<212> TYPE: PRT
<213> ORGANISM: Borrelia sp.

<400> SEQUENCE: 12
```

Gln Ala Ile Val Glu Thr Gly Lys Phe Leu Lys Ile Glu Glu Glu
1               5                   10                  15

Ala Leu Lys Leu Lys Glu Thr Gly Asn
                20                  25

<210> SEQ ID NO 13
<211> LENGTH: 25
<212> TYPE: PRT
<213> ORGANISM: Borrelia sp.

<400> SEQUENCE: 13

Glu Ala Leu Lys Leu Lys Glu Thr Gly Asn Ser Gly Gln Phe Leu Ala
1               5                   10                  15

Met Phe Asp Leu Met Leu Glu Val Val
                20                  25

<210> SEQ ID NO 14
<211> LENGTH: 25
<212> TYPE: PRT
<213> ORGANISM: Borrelia sp.

<400> SEQUENCE: 14

Ala Met Phe Asp Leu Met Leu Glu Val Val Glu Ser Leu Glu Asp Val
1               5                   10                  15

Gly Ile Ile Gly Leu Lys Ala Arg Val
20 25

<210> SEQ ID NO 15
<211> LENGTH: 25
<212> TYPE: PRT
<213> ORGANISM: Borrelia sp.

<400> SEQUENCE: 15

Val Gly Ile Ile Gly Leu Lys Ala Arg Val Leu Glu Glu Ser Lys Asn
1 5 10 15

Asn Pro Ile Asn Thr Ala Glu Arg Leu
20 25

<210> SEQ ID NO 16
<211> LENGTH: 25
<212> TYPE: PRT
<213> ORGANISM: Borrelia sp.

<400> SEQUENCE: 16

Asn Asn Pro Ile Asn Thr Ala Glu Arg Leu Leu Ala Ala Lys Ala Gln
1 5 10 15

Ile Glu Asn Gln Leu Lys Val Val Lys
20 25

<210> SEQ ID NO 17
<211> LENGTH: 25
<212> TYPE: PRT
<213> ORGANISM: Borrelia sp.

<400> SEQUENCE: 17

Gln Ile Glu Asn Gln Leu Lys Val Val Lys Glu Lys Gln Asn Ile Glu
1 5 10 15

Asn Gly Gly Glu Lys Lys Asn Asn Lys
20 25

<210> SEQ ID NO 18

```
<211> LENGTH: 25
<212> TYPE: PRT
<213> ORGANISM: Borrelia sp.

<400> SEQUENCE: 18

Leu Lys Val Val Lys Glu Lys Gln Asn Ile Glu Asn Gly Gly Glu Lys
1               5                   10                  15

Lys Asn Asn Lys Ser Lys Lys Lys Lys
            20                  25

<210> SEQ ID NO 19
<211> LENGTH: 25
<212> TYPE: PRT
<213> ORGANISM: Borrelia sp.

<400> SEQUENCE: 19

Phe Gly Leu Ser Gly Ala Tyr Gly Asn Glu Thr Phe Asn Asn Ser Ser
1               5                   10                  15

Ile Thr Tyr Ser Leu Lys Asp Lys Ser
            20                  25

<210> SEQ ID NO 20
<211> LENGTH: 25
<212> TYPE: PRT
<213> ORGANISM: Borrelia sp.

<400> SEQUENCE: 20

Ser Ile Thr Tyr Ser Leu Lys Asp Lys Ser Val Val Gly Asn Asp Leu
1               5                   10                  15

Leu Ser Pro Thr Leu Ser Asn Ser Ala
            20                  25

<210> SEQ ID NO 21
<211> LENGTH: 25
<212> TYPE: PRT
<213> ORGANISM: Borrelia sp.

<400> SEQUENCE: 21

Leu Leu Ser Pro Thr Leu Ser Asn Ser Ala Ile Leu Ala Ser Phe Gly
1               5                   10                  15

Ala Lys Tyr Lys Leu Gly Leu Thr Lys
            20                  25

<210> SEQ ID NO 22
<211> LENGTH: 20
<212> TYPE: PRT
<213> ORGANISM: Borrelia sp.

<400> SEQUENCE: 22

Gly Ala Lys Tyr Lys Leu Gly Leu Thr Lys Ile Asn Asp Lys Asn Thr
1               5                   10                  15

Tyr Leu Ile Leu
            20

<210> SEQ ID NO 23
<211> LENGTH: 20
<212> TYPE: PRT
<213> ORGANISM: Borrelia sp.

<400> SEQUENCE: 23

Leu Gly Leu Thr Lys Ile Asn Asp Lys Asn Thr Tyr Leu Ile Leu Gln
1               5                   10                  15
```

Met Gly Thr Asp
            20

<210> SEQ ID NO 24
<211> LENGTH: 20
<212> TYPE: PRT
<213> ORGANISM: Borrelia sp.

<400> SEQUENCE: 24

Thr Tyr Leu Ile Leu Gln Met Gly Thr Asp Phe Gly Ile Asp Pro Phe
1               5                   10                  15

Ala Ser Asp Phe
            20

<210> SEQ ID NO 25
<211> LENGTH: 20
<212> TYPE: PRT
<213> ORGANISM: Borrelia sp.

<400> SEQUENCE: 25

Gln Met Gly Thr Asp Phe Gly Ile Asp Pro Phe Ala Ser Asp Phe Ser
1               5                   10                  15

Ile Phe Gly His
            20

<210> SEQ ID NO 26
<211> LENGTH: 25
<212> TYPE: PRT
<213> ORGANISM: Borrelia sp.

<400> SEQUENCE: 26

Phe Ala Ser Asp Phe Ser Ile Phe Gly His Ile Ser Lys Ala Ala Asn
1               5                   10                  15

Phe Lys Lys Glu Thr Pro Ser Asp Pro
            20                  25

<210> SEQ ID NO 27
<211> LENGTH: 25
<212> TYPE: PRT
<213> ORGANISM: Borrelia sp.

<400> SEQUENCE: 27

Asn Phe Lys Lys Glu Thr Pro Ser Asp Pro Asn Lys Lys Ala Glu Ile
1               5                   10                  15

Phe Asp Pro Asn Gly Asn Ala Leu Asn
            20                  25

<210> SEQ ID NO 28
<211> LENGTH: 25
<212> TYPE: PRT
<213> ORGANISM: Borrelia sp.

<400> SEQUENCE: 28

Ile Phe Asp Pro Asn Gly Asn Ala Leu Asn Phe Ser Lys Asn Thr Glu
1               5                   10                  15

Leu Gly Ile Ala Phe Ser Thr Gly Ala
            20                  25

<210> SEQ ID NO 29
<211> LENGTH: 20
<212> TYPE: PRT
<213> ORGANISM: Borrelia sp.

-continued

```
<400> SEQUENCE: 29

Glu Leu Gly Ile Ala Phe Ser Thr Gly Ala Ser Ile Gly Phe Ala Trp
1               5                   10                  15

Asn Lys Asp Thr
            20

<210> SEQ ID NO 30
<211> LENGTH: 20
<212> TYPE: PRT
<213> ORGANISM: Borrelia sp.

<400> SEQUENCE: 30

Phe Ser Thr Gly Ala Ser Ile Gly Phe Ala Trp Asn Lys Asp Thr Gly
1               5                   10                  15

Glu Lys Glu Ser
            20

<210> SEQ ID NO 31
<211> LENGTH: 25
<212> TYPE: PRT
<213> ORGANISM: Borrelia sp.

<400> SEQUENCE: 31

Phe Ser Thr Gly Ala Ser Ile Gly Phe Ala Trp Asn Lys Asp Thr Gly
1               5                   10                  15

Glu Lys Glu Ser Trp Ala Ile Lys Gly
            20                  25

<210> SEQ ID NO 32
<211> LENGTH: 15
<212> TYPE: PRT
<213> ORGANISM: Borrelia sp.

<400> SEQUENCE: 32

Lys Glu Met Leu Ala Asn Ser Val Lys Glu Leu Thr Ser Pro Ile
1               5                   10                  15

<210> SEQ ID NO 33
<211> LENGTH: 21
<212> TYPE: PRT
<213> ORGANISM: Borrelia sp.

<400> SEQUENCE: 33

Ala Thr Lys Ala Ile Gly Lys Lys Ile Gln Gln Asn Gly Gly Leu Ala
1               5                   10                  15

Val Glu Ala Gly His
            20

<210> SEQ ID NO 34
<211> LENGTH: 40
<212> TYPE: PRT
<213> ORGANISM: Borrelia burgdorferi

<400> SEQUENCE: 34

Asn Val Arg Thr Ala Glu Glu Leu Gly Met Gln Pro Ala Lys Ile Asn
1               5                   10                  15

Thr Pro Ala Ser Leu Ser Gly Ser Gln Ala Ser Trp Thr Leu Arg Val
            20                  25                  30

His Val Gly Ala Asn Gln Asp Glu
        35                  40
```

```
<210> SEQ ID NO 35
<211> LENGTH: 20
<212> TYPE: PRT
<213> ORGANISM: Borrelia burgdorferi

<400> SEQUENCE: 35

Gln Asp Glu Ala Ile Ala Val Asn Ile Tyr Ala Ala Asn Val Ala Asn
1               5                   10                  15

Leu Phe Ser Gly
            20

<210> SEQ ID NO 36
<211> LENGTH: 19
<212> TYPE: PRT
<213> ORGANISM: Borrelia burgdorferi

<400> SEQUENCE: 36

Ser Leu Ala Lys Ile Glu Asn Ala Ile Arg Met Ile Ser Asp Gln Arg
1               5                   10                  15

Ala Asn Leu

<210> SEQ ID NO 37
<211> LENGTH: 180
<212> TYPE: PRT
<213> ORGANISM: Borrelia burgdorferi

<400> SEQUENCE: 37

Ser Ile Val Met Val Leu Phe Phe Asp Leu Leu Val Ala Cys Ser Ile
1               5                   10                  15

Gly Leu Val Glu Arg Thr Asn Ala Ala Leu Glu Ser Ser Ser Lys Asp
            20                  25                  30

Leu Lys Asn Lys Ile Leu Lys Ile Lys Lys Glu Ala Thr Gly Lys Gly
        35                  40                  45

Val Leu Phe Glu Ala Phe Thr Gly Leu Lys Thr Gly Ser Lys Val Thr
    50                  55                  60

Ser Gly Gly Leu Ala Leu Arg Glu Ala Lys Val Gln Ala Ile Val Glu
65                  70                  75                  80

Thr Gly Lys Phe Leu Lys Ile Ile Glu Glu Ala Leu Lys Leu Lys
                85                  90                  95

Glu Thr Gly Asn Ser Gly Gln Phe Leu Ala Met Phe Asp Leu Met Leu
            100                 105                 110

Glu Val Val Glu Ser Leu Glu Asp Val Gly Ile Ile Gly Leu Lys Ala
        115                 120                 125

Arg Val Leu Glu Glu Ser Lys Asn Asn Pro Ile Asn Thr Ala Glu Arg
    130                 135                 140

Leu Leu Ala Ala Lys Ala Gln Ile Glu Asn Gln Leu Lys Val Val Lys
145                 150                 155                 160

Glu Lys Gln Asn Ile Glu Asn Gly Gly Glu Lys Lys Asn Asn Lys Ser
                165                 170                 175

Lys Lys Lys Lys
            180

<210> SEQ ID NO 38
<211> LENGTH: 150
<212> TYPE: PRT
<213> ORGANISM: Borrelia burgdorferi

<400> SEQUENCE: 38

Phe Gly Leu Ser Gly Ala Tyr Gly Asn Glu Thr Phe Asn Asn Ser Ser
```

```
                1               5                    10                   15
            Ile Thr Tyr Ser Leu Lys Asp Lys Ser Val Val Gly Asn Asp Leu Leu
                            20                  25                  30

Ser Pro Thr Leu Ser Asn Ser Ala Ile Leu Ala Ser Phe Gly Ala Lys
                        35                  40                  45

Tyr Lys Leu Gly Leu Thr Lys Ile Asn Asp Lys Asn Thr Tyr Leu Ile
                50                  55                  60

Leu Gln Met Gly Thr Asp Phe Gly Ile Asp Pro Phe Ala Ser Asp Phe
            65                  70                  75                  80

Ser Ile Phe Gly His Ile Ser Lys Ala Ala Asn Phe Lys Lys Glu Thr
                            85                  90                  95

Pro Ser Asp Pro Asn Lys Lys Ala Glu Ile Phe Asp Pro Asn Gly Asn
                        100                 105                 110

Ala Leu Asn Phe Ser Lys Asn Thr Glu Leu Gly Ile Ala Phe Ser Thr
                        115                 120                 125

Gly Ala Ser Ile Gly Phe Ala Trp Asn Lys Asp Thr Gly Glu Lys Glu
                        130                 135                 140

Ser Trp Ala Ile Lys Gly
            145                 150

<210> SEQ ID NO 39
            <211> LENGTH: 21
            <212> TYPE: PRT
            <213> ORGANISM: Borrelia burgdorferi

<400> SEQUENCE: 39

Ala Thr Lys Ala Ile Gly Lys Lys Ile Gln Gln Asn Gly Gly Leu Ala
            1               5                   10                  15

Val Glu Ala Gly His
                        20

<210> SEQ ID NO 40
            <211> LENGTH: 15
            <212> TYPE: PRT
            <213> ORGANISM: Borrelia burgdorferi

<400> SEQUENCE: 40

Lys Glu Met Leu Ala Asn Ser Val Lys Glu Leu Thr Ser Pro Ile
            1               5                   10                  15
```

COMPOSITIONS AND METHODS FOR DIAGNOSING LYME DISEASE AND FOR PREDICTING LYME DISEASE SPIROCHETE ELIMINATION AFTER TREATMENT

STATEMENT REGARDING SEQUENCE LISTING

The Sequence Listing associated with this application is provided in text format in lieu of a paper copy, and is hereby incorporated by reference into the specification. The name of the text file containing the Sequence Listing is 770025_466USPC_SEQUENCE-LISTING. The text file is 12.2 KB, was created on Mar. 23, 2018, and is being submitted electronically via EFS-Web.

BACKGROUND

Technical Field

The present disclosure relates generally to compositions and methods for diagnosing Lyme disease and for assessing the efficacy of a Lyme disease treatment. More specifically, there are provided combinations of multiple T-cell epitope-containing peptides derived from distinct *Borrelia* polypeptide antigens that are expressed at different stages of Lyme disease, for use in a sensitive secondary in vitro immune response assay for *Borrelia*-specific T-cell responsiveness.

Description of the Related Art

Lyme disease is a tick-borne infectious disease caused by pathogenic spirochetes of the genus *Borrelia*, including *B. burgdorferi*, *B. afzelii*, *B. garinii*, and other *Borrelia* spp. The infectious microorganisms are transmitted from tick saliva into bite wounds and the "early localized" stage, the first of three clinically defined stages of disease, typically appears within two weeks of the tick bite. The early localized stage is often but not always accompanied by erythema migrans (EM), an erythematous skin lesion at the site of the tick bite. The disease progresses to the second, "early disseminated" stage as the infectious *Borrelia* bacteria spread systemically via blood and/or lymphatic circulation, and may be accompanied by one or more of additional skin lesions, fatigue, myalgia, arthralgia, neurologic and cardiac symptoms. Untreated, the disease may progress further to "late stage" Lyme disease, characterized by arthritis, encephalomyelitis and/or peripheral neuropathy, and potentially other symptoms including chronic Lyme disease. Approximately 25,000 to 30,000 cases of Lyme disease are reported in the United States annually, with CDC estimates of actual incidence reaching ten times that amount in view of underreporting; additional cases have also been reported in Europe and Asia (Wright et al., 2012 *Am. Fam. Physician* 85:1086; Shapiro, 2014 *N. Engl. J. Med.* 370:1724).

Altered patterns of expression of *Borrelia* spp. antigenic proteins accompany the course of Lyme disease progression and are believed to underlie immune evasion mechanisms that may account for chronic Lyme disease (e.g., Drecktrah et al., 2013 *PLoS One* 8(7):e68799; Schmit et al., 2011 *Front. Microbiol.* 2:141; Salo et al., 2011 *J. Infect. Dis.* 204:65; Liang et al., 2004 *Infect. Immun.* 72:5759; Aberer, 2007 *J. Dtsch. Dermatol. Ges.* 5(5):406).

Effective treatment of Lyme disease (LD) depends on accurate detection of early infection with *Borrelia* spp. In some instances, when the disease is still in the early local stage, the presence of the characteristic erythema migrans (EM) skin lesion is sufficient for accurate diagnosis (e.g., Nadelman et al., 1996 *Am J Med* 100:502-508). Significant numbers of patients, however, fail to develop the EM lesion, or the rash remains undetected or is misidentified. In these instances, traditional serologic testing to detect anti-*Borrelia* IgM and/or IgG antibody responses is the most widely-used procedure to confirm the illness (e.g., Dattwyler et al., 2010 *Clin Infect Dis* 50:521-522; Johnson et al., 1996 *J. Infect. Dis.* 174:346).

There is currently no laboratory test capable of reliably predicting successful treatment of LD following administration of a standard therapeutic course (e.g., antibiotic regimen). Circulating antibodies that have been elicited by a *Borrelia* infection may persist for years, even following successful antibiotic therapy to clear the infection. Testing for *Borrelia*-specific antibodies is therefore of limited usefulness, for instance, because *Borrelia* spp. spirochetes can colonize multiple mammalian tissues and cause numerous non-specific clinical abnormalities such as joint and/or muscle aches or general malaise. These symptoms may be difficult to distinguish from similar clinical presentations that are not due to a persistent *Borrelia* infection, resulting in considerable confusion and increased healthcare costs. It would therefore be extremely useful to be able to clinically confirm effective elimination of pathogenic *Borrelia* spp. spirochetes following treatment for LD.

WO 2013/116668 describes peptide antigens that are recognized by antibodies that have been generated in response to *Borrelia* spp. However, anti-*Borrelia* antibodies are typically not produced at detectable levels for several weeks after infection, so many early cases of LD are missed. As also noted above, the levels of antibodies that are produced in response to an infection with Lyme disease spirochetes can remain elevated for years following infection, even following successful treatment such as antibiotic treatment that eliminates *Borrelia* spirochetes. Determination of anti-*Borrelia* antibody responses therefore suffer from poor sensitivity and unreliability as diagnostic tests for pathogenic *Borrelia* spp., and are of little use as prognostic tests following treatment for a *Borrelia* infection.

*Borrelia* infections can also elicit a T-cell immune response. Glickstein et al. (2003 *Infect. Immun.* 71:6051) and Dattwyler et al. (1988 *N. Engl. J. Med.* 319:1441) demonstrated that human subjects exposed to *Borrelia burgdorferi* developed a vigorous and sustained T-cell response, evidenced by the presence of inflammatory cytokines accompanying EM at the early local stage of disease. This T-cell response preceded any detectably measurable antibody response. For instance, T-cells activated in response to Lyme disease spirochetes reliably produced interferon-γ (Ekerfelt et al., 1999 *Clin Exp. Immunol.* 115:498; Sikand et al., 1999 *Clin. Diagnost. Lab. Immunol.* 6:445). Activated T-cells appeared with the same incidence in two patient populations: (i) those who presented clinically with no LD symptoms but in whom circulating anti-*Borrelia* antibodies were detectable, and (ii) patients who exhibited the characteristic clinical signs of *Borrelia* infection (i.e., LD symptoms)(Ekerfelt et al., 1999). WO 2012/039614 describes in vitro T-cell cytokine responses that were elicited by peripheral white blood cells from a *Borrelia*-infected individual following incubation with whole, fixed, or crudely fractionated *Borrelia* cells. In WO 2012/039614, however, no disclosure can be found that identifies any particular stage of a *Borrelia* infection (e.g., early local, early disseminated, late disseminated) at which the *Borrelia* pathogen might be recognized by T-cells, nor any particular *Borrelia* antigens that are capable of eliciting such responses, nor the structures of any *Borrelia* antigenic epitopes that are recognized by T-cells. The significance and specificity of T-cell immune responses in early LD thus remains unclear, in particular, where no specific *Borrelia* spp. antigens that are recognized by T-cells have been identified in the pathogenesis of LD, and where no *Borrelia*-specific T-cell epitopes are known.

Clearly there remains a need for improved diagnostic and prognostic assessment of Lyme disease, including early and more sensitive detection of LD, and the ability to monitor the therapeutic efficacy of an administered treatment for LD. The presently disclosed invention embodiments address these needs and offer other related advantages.

BRIEF SUMMARY

According to certain embodiments of the invention that is disclosed herein, there is provided a composition for diagnosis or prognosis of Lyme disease that is selected from a first composition and a second composition: (I) the first composition comprising: (a) 1, 2, 3, 4, or 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 1, 2, 3, 4, 5, 6, 7, 8, 9, 10, 11, 12, or 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 1, 2, 3, 4, 5, 6, 7, 8, 9, 10, 11, 12, or 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 1 or 2 isolated OspC peptides that each comprise a *Borrelia* T-cell epitope and are selected from the OspC peptides having the amino acid sequences set forth in SEQ ID NO:32-33, or one or more variants thereof having at least 80% amino acid sequence identity to the amino acid sequences set forth in SEQ ID NOS:32-33, wherein the composition, after being contacted with whole blood obtained from a subject infected with a *Borrelia* species associated with Lyme disease, is capable of eliciting a secondary in vitro immune response by T-cells; and (II) the second composition comprising: (a) 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 2 isolated OspC peptides that each comprise a *Borrelia* T-cell epitope and are selected from the OspC peptides having the amino acid sequences set forth in SEQ ID NOS:32-33, or one or more variants thereof having at least 80% amino acid sequence identity to the amino acid sequences set forth in SEQ ID NOS:32-33.

In certain further embodiments, at least one of: (a) the composition comprises at least about one nanogram of each peptide and not more than about 100 nanograms of each peptide, (b) the composition comprises at least about 100, 200, 300, or 400 nanograms and not more than about 500 nanograms of each peptide, (c) the composition comprises at least about 500, 600, 700, 800, or 900 nanograms and not more than about 1000 nanograms of each peptide, (d) the composition comprises at least about 1.0, 1.1, 1.2, 1.3, 1.4, 1.5, 1.6, 1.7, 1.8, or 1.9 micrograms and not more than about 2 micrograms of each peptide, or (e) the composition comprises at least about 1, 2, 3, 4, 5, 6, 7, 8, or 9 micrograms and not more than about 10 micrograms of each peptide.

In another embodiment of the present invention there is provided a method for detecting Lyme disease in a subject, or for monitoring efficacy of a treatment for Lyme disease in a subject, comprising: (A) contacting in vitro (i) a first biological sample obtained at a first timepoint a subject known to have or suspected of being at risk for having Lyme disease, wherein the biological sample comprises T-cells and antigen-presenting cells, and (ii) a peptide composition for diagnosis or prognosis of Lyme disease, to obtain a first test incubation mixture; (B) incubating the first test incubation mixture under conditions and for a time sufficient for specific recognition by said T-cells of a *Borrelia* T-cell epitope that is present in said peptide composition to stimulate generation of a T-cell immune response indicator; and (C) detecting a first level of the T-cell immune response indicator in the first test incubation mixture, wherein presence of a *Borrelia* infection in the subject is indicated by detection in (C) of said first level of the T-cell immune response indicator that is increased relative to a first control level of the T-cell immune response indicator obtained by incubating the first biological sample in a first control incubation without the peptide composition for diagnosis or prognosis of Lyme disease, and wherein the peptide composition for diagnosis or prognosis of Lyme disease comprises: (a) 1, 2, 3, 4, or 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 1, 2, 3, 4, 5, 6, 7, 8, 9, 10, 11, 12, or 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 1, 2, 3, 4, 5, 6, 7, 8, 9, 10, 11, 12, or 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 1 or 2 isolated OspC peptides that each comprise a *Borrelia* T-cell epitope and are selected from the OspC peptides having the amino acid sequences set forth in SEQ ID NO:32-33, or one or more variants thereof having at least 80% amino acid sequence identity to the amino acid sequences set forth in SEQ ID NOS:32-33, and thereby detecting Lyme disease in the subject, or monitoring efficacy of the treatment for Lyme disease in the subject.

In certain further embodiments the first timepoint is prior to administration to the subject of treatment for Lyme disease.

In certain related embodiments the peptide composition for diagnosis or prognosis of Lyme disease comprises: (a) 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 2 isolated OspC peptides that each comprise a *Borrelia* T-cell epitope and are selected from the OspC peptides having the amino acid sequences set forth in SEQ ID NOS:32-33, or one or more variants thereof having at least 80% amino acid sequence identity to the amino acid sequences set forth in SEQ ID NOS:32-33.

In certain further embodiments of the above described methods, the method further comprises (D) contacting in vitro (i) a second biological sample obtained from the subject at a second timepoint that is later than the first timepoint and is after administration to the subject of treatment for Lyme disease, wherein the second biological sample comprises T-cells and antigen-presenting cells, and (ii) the peptide composition for diagnosis or prognosis of Lyme disease, to obtain a second test incubation mixture; (E) incubating the second test incubation mixture under conditions and for a time sufficient for specific recognition by said T-cells of a *Borrelia* T-cell epitope that is present in said peptide composition to stimulate generation of a T-cell immune response indicator; and (F) detecting a second level of the T-cell immune response indicator in the second test incubation mixture, wherein presence of a *Borrelia* infection in the subject is indicated by detection in (F) of said second level of the T-cell immune response indicator that is increased relative to a second control level of the T-cell immune response indicator obtained by incubating the second biological sample in a second control incubation without the peptide composition for diagnosis or prognosis of Lyme disease, and wherein efficacy of the treatment for Lyme disease is indicated by detection in (F) of said second level of the T-cell immune response indicator that is decreased relative to the first level of the T-cell immune response indicator that is detected in (C).

In certain still further embodiments, the peptide composition for diagnosis or prognosis of Lyme disease comprises: (a) 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 2 isolated OspC peptides that each comprise a *Borrelia* T-cell epitope and are selected from the OspC peptides having the amino acid sequences set forth in SEQ ID NOS:32-33, or one or more variants thereof having at least 80% amino acid sequence identity to the amino acid sequences set forth in SEQ ID NOS:32-33.

In certain embodiments of any of the above described methods, Lyme disease comprises an infection with at least one pathogenic *Borrelia* species, and in certain further embodiments the pathogenic *Borrelia* species is pathogenic in humans. In certain still further embodiments the *Borrelia* species that is pathogenic in humans is selected from *Borrelia burgdorferi, Borrelia burgdorferi sensu stricto, Borrelia azfelii, Borrelia garinii, Borrelia valaisiana, Borrelia spielmanii, Borrelia bissettii, Borrelia lusitaniae*, and *Borrelia bavariensis*.

In certain embodiments of any of the above described methods, the treatment for Lyme disease comprises administering an antibiotic to the subject. In certain further embodiments the antibiotic is selected from tetracyclines; oxytetracycline, tetracycline, doxycycline, or minocycline; penicillins; amoxicillin or penicillin; cephalosporins; cefaclor, cefbuperazone, cefminox, cefotaxime, cefotetan, cefmetazole, cefoxitin, cefuroxime axetil, cefuroxime acetyl, ceftin, or ceftriaxone; macrolides; azithromycin, clarithromycin, or erythromycin.

In certain embodiments of any of the above described methods, the biological sample comprises at least one of whole blood, cerebrospinal fluid, or synovial fluid. In certain embodiments of any of the above described methods, the biological sample comprises at least one of (a) whole blood, (b) a cellular fraction of whole blood, (c) isolated peripheral blood white cells, or (d) isolated peripheral blood mononuclear cells.

In certain embodiments of any of the above described methods, the T-cell immune response indicator is interferon-gamma (IFN-γ). In certain further embodiments the IFN-γ is soluble IFN-γ released by the T-cells. In certain embodiments of any of the above described methods, the T-cell immune response indicator comprises at least one of T-cell proliferation and expression of a T-cell cytokine. In certain further embodiments the T-cell cytokine is selected from IL-1α, IL-1β, IL-2, IL-10, IL-12, IL-17, TNF-α, TNF-β, and IFN-γ. In certain embodiments expression of the T-cell cytokine is detected as soluble T-cell cytokine released by the T-cells. In certain further embodiments the T-cell cytokine is selected from IL-1α, IL-1β, IL-2, IL-10, IL-12, IL-17, TNF-α, TNF-β, and IFN-γ. In certain embodiments the T-cell cytokine is detected by determining detectable specific binding of a binding agent to the T-cell cytokine. In certain further embodiments the binding agent comprises at least one antibody that binds specifically to the T-cell cytokine. In certain further embodiments the at least one antibody is selected from a monoclonal antibody and a polyclonal antibody. In certain embodiments the at least one antibody is immobilized on a solid phase.

In certain embodiments of any of the above described methods, Lyme disease comprises an infection with at least one pathogenic *Borrelia* species. In certain embodiments the pathogenic *Borrelia* species is pathogenic in humans. In certain further embodiments the *Borrelia* species that is pathogenic in humans is selected from *Borrelia burgdorferi*, *Borrelia burgdorferi* sensu stricto, *Borrelia azfelii*, *Borrelia garinii*, *Borrelia valaisiana*, *Borrelia spielmanii*, *Borrelia bissettii*, *Borrelia lusitaniae*, and *Borrelia bavariensis*.

In certain further embodiments of the above described methods (e.g., those that include steps (D)-(F) relating to a second biological sample) the treatment for Lyme disease comprises administering an antibiotic to the subject. In certain further embodiments the antibiotic is selected from tetracyclines; oxytetracycline, tetracycline, doxycycline, or minocycline; penicillins; amoxicillin or penicillin; cephalosporins; cefaclor, cefbuperazone, cefminox, cefotaxime, cefotetan, cefmetazole, cefoxitin, cefuroxime axetil, cefuroxime acetyl, ceftin, or ceftriaxone; macrolides; azithromycin, clarithromycin, or erythromycin. In certain embodiments the biological sample comprises at least one of whole blood, cerebrospinal fluid, or synovial fluid. In certain embodiments the biological sample comprises at least one of (a) whole blood, (b) a cellular fraction of whole blood, (c) isolated peripheral blood white cells, or (d) isolated peripheral blood mononuclear cells. In certain embodiments the T-cell immune response indicator is interferon-gamma (IFN-γ), which in certain further embodiments is soluble IFN-γ released by the T-cells. In certain embodiments the T-cell immune response indicator comprises at least one of T-cell proliferation and expression of a T-cell cytokine, which in certain further embodiments is selected from IL-1α, IL-1β, IL-2, IL-10, IL-12, IL-17, TNF-α, TNF-β, and IFN-γ. In certain embodiments expression of the T-cell cytokine is detected as soluble T-cell cytokine released by the T-cells. In certain embodiments the T-cell cytokine is selected from IL-1α, IL-1β, IL-2, IL-10, IL-12, IL-17, TNF-α, TNF-β, and IFN-γ. In certain further embodiments the T-cell cytokine is detected by determining detectable specific binding of a binding agent to the T-cell cytokine. In certain further embodiments the binding agent comprises at least one antibody that binds specifically to the T-cell cytokine. In certain further embodiments the at least one antibody is selected from a monoclonal antibody and a polyclonal antibody. In certain further embodiments the at least one antibody is immobilized on a solid phase. In certain further embodiments the method comprises repeating steps (D), (E), and (F) at a plurality of second timepoints that are different from one another and that are later than the first timepoint and after administration to the subject of the treatment for Lyme disease. In certain further embodiments the plurality of second timepoints comprises 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 timepoints.

Turning to another embodiment there is provided a composition that is selected from a first nucleic acid composition and a second nucleic acid composition: (I) the first nucleic acid composition comprising one or a plurality of isolated nucleic acid molecules that encode: (a) 1, 2, 3, 4, or 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 1, 2, 3, 4, 5, 6, 7, 8, 9, 10, 11, 12, or 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 1, 2, 3, 4, 5, 6, 7, 8, 9, 10, 11, 12, or 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 1 or 2 isolated OspC peptides that each comprise a *Borrelia* T-cell epitope and are selected from the OspC peptides having the amino acid sequences set forth in SEQ ID NO:32-33, or one or more variants thereof having at least 80% amino acid sequence identity to the amino acid sequences set forth in SEQ ID NOS:32-33, wherein the FlaB, DbpB, p66 and OspC peptides, after being contacted with whole blood obtained from a subject infected with a *Borrelia* species associated with Lyme disease, are capable of eliciting a secondary in vitro immune response by T-cells; and (II) the second nucleic acid composition comprising one or a plurality of isolated nucleic acid molecules that encode: (a) 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 2 isolated OspC peptides that each comprise a *Borrelia* T-cell epitope and are selected from the OspC peptides having the amino acid sequences set forth in SEQ ID NOS:32-33, or one or more variants thereof having at least 80% amino acid sequence identity to the amino acid sequences set forth in SEQ ID NOS:32-33, wherein the FlaB, DbpB, p66 and OspC peptides, after being contacted with whole blood obtained from a subject infected with a *Borrelia* species associated with Lyme disease, are capable of eliciting a secondary in vitro immune response by T-cells. In another embodiment there is provided a vector composition comprising one or more nucleic acid vectors that comprise the above described first nucleic acid composition and/or the above described second nucleic acid composition. In another embodiment there is provided a host cell comprising the above-described vector composition.

These and other aspects and embodiments of the invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet, are incorporated herein by reference in their entirety, as if each was incorporated individually. Aspects and embodiments of the invention can be modified, if necessary, to employ concepts of the various patents, applications and publications to provide yet further embodiments of the invention.

BRIEF DESCRIPTION OF THE SEVERAL VIEWS OF THE DRAWINGS

FIG. 1 shows detection of IFN-γ after secondary in vitro T-cell activation with a peptide pool (SEQ ID NOS:1-33) in blood samples collected before and approximately 60 days post-treatment.

DETAILED DESCRIPTION

The presently disclosed invention embodiments relate to an artificial composition that permits surprisingly sensitive diagnosis and prognosis of Lyme disease (LD), and that comprises a non-naturally occurring combination of defined peptides. As described herein, there is thus provided a composition comprising a combination of peptides that includes one or more peptide from each of the presently disclosed pathogenic *Borrelia* spp.-derived peptide regions of flagellin (FlaB) [SEQ ID NOS:1-5], decorin binding protein (DbpB) [SEQ ID NOS:6-18], common antigen (p66) [SEQ ID NOS; 19-31], and outer surface protein C (OspC) [SEQ ID NOS:32-33], or variant peptides thereof. Each peptide contains a *Borrelia* spp.-specific T-cell epitope, as disclosed for the first time herein. Related methods are also provided, including methods for diagnosing Lyme disease in a subject, and for monitoring clearance of pathogenic *Borrelia* spp. microorganisms following treatment of the subject.

The presently described combinations of peptides do not occur naturally, given that FlaB, DbpB, p66, and OspC are known to be expressed at different stages in the progression of Lyme disease (typically referred to as the early local, early disseminated, and late disseminated stages) and so would not naturally be concomitantly exposed to an infected host's immune system. For example, OspC is expressed by *Borrelia* bacteria during the early local stage of infection, DbpB and p66 are expressed after dissemination of the *Borrelia* infection, and FlaB is expressed during the late disseminated and early local stages. The presently disclosed peptide cocktail may also contain artificial peptides that differ from the naturally processed *Borrelia* spp. antigen fragments that are displayed by antigen-presenting cells in vivo. Furthermore, the presently disclosed FlaB, DbpB, p66, and OspC peptides are not all found naturally in a single pathogenic *Borrelia* species and therefore would not have been expected to have been encountered by the immune system of a single Lyme disease patient. Accordingly, the present embodiments unexpectedly permit early detection of Lyme disease in a wide range of subjects having or suspected of having Lyme disease, which can be achieved by detecting a secondary in vitro response to the present compositions by T-cells from such subjects.

As described below, for example, all samples containing T-cells from LD subjects responded to at least one peptide from at least one of the herein described FlaB, DbpB, p66, and OspC *Borrelia* T-cell epitope-containing polypeptides (see Tables 1 and 2), even where T-cells of certain samples did not respond to peptides from all four of FlaB, DbpB, p66, and OspC. Moreover, all samples containing T-cells from LD subjects responded to a peptide cocktail containing at least one peptide from all four of FlaB, DbpB, p66, and OspC. Hence, according to non-limiting theory, the present embodiments permit rapid and sensitive detection of *Borrelia* spp.-specific T-cells in a sample regardless of the particular *Borrelia* spp. pathogen with which a subject may be infected, and regardless of the stage of disease progression (early local, early disseminated, or late disseminated) from which the T-cells have been obtained. The present embodiments further permit detection of *Borrelia* spp.-specific T-cells in a sample even in cases where it is unknown whether the subject has LD, by unprecedentedly providing a combination of *Borrelia* T-cell epitope-containing peptides that includes representative epitopes present at all stages of Lyme disease progression. The presently disclosed embodiments are useful in the detection of Lyme disease that may result from infection by any of a variety of *Borrelia* species that are pathogenic, such as *Borrelia* species that are pathogenic in humans, including *Borrelia burgdorferi*, *Borrelia burgdorferi* sensu stricto, *Borrelia azfelii*, *Borrelia garinii*, *Borrelia valaisiana*, *Borrelia spielmanii*, *Borrelia bissettii*, *Borrelia lusitaniae*, and *Borrelia bavariensis*. (See, e.g., (Wright et al., 2012 *Am. Fam. Physician* 85:1086; Shapiro, 2014 *N. Engl. J. Med.* 370:1724; Schutzer et al., 2012 *J. Bacteriol.* 194(2):545).

As described herein, the present compositions, comprising the combination of at least one of the disclosed *Borrelia* spp. T-cell epitope-containing peptides from each of FlaB, DbpB, p66, and OspC (e.g., SEQ ID NOS:1-33 as set forth in Table 2), possess properties that are markedly different from those of any individual constituent peptide or of any subset of concomitantly expressed peptides that does not include at least one each of a FlaB [SEQ ID NOS:1-5], a DbpB [SEQ ID NOS:6-18], a p66 [SEQ ID NOS:19-31], and an OspC [SEQ ID NOS:32-33] peptide as provided herein. The present compositions surprisingly elicit more robust secondary in vitro immune responses by T-cells from LD-afflicted subjects (including early-stage LD) than do any of the individual constituent peptides (or incomplete subsets that lack at least one of a FlaB, a DbpB, a p66, or an OspC peptide), thereby providing unprecedented sensitivity for the detection, including early detection, of LD. Hence, by facilitating earlier detection of LD than can be achieved merely by assaying a secondary in vitro T-cell response to any of the individual constituent peptides described herein (or to an incomplete peptide subset that contains only peptides derived from concomitantly expressed *Borrelia* spp. polypeptides but which lacks at least one of a FlaB, a DbpB, a p66, or an OspC peptide), the present embodiments provide significantly more than can be achieved using any naturally occurring subcombinations of *Borrelia* spp. polypeptides.

Accordingly, the presently disclosed compositions comprise *Borrelia* spp. FlaB, DbpB, p66, and OspC peptides or variants thereof that contain *Borrelia*-specific T-cell epitopes in combinations that do not occur naturally, and in certain embodiments, the presently disclosed compositions comprise *Borrelia* spp. FlaB, DbpB, p66, and OspC peptides or variants thereof in non-naturally occurring quantities relative to one another, thereby (and further according to non-limiting theory) to achieve certain of the herein described advantages.

There is thus disclosed herein an alternative approach to any approach previously known for confirming the presence of Lyme disease (LD) in a subject having or suspected of having LD, by providing a test that detects an immune response indicator (e.g., interferon-γ) produced by T-cells that have been activated by exposure to specific regions within individual Lyme disease spirochete proteins. Specific T-cell reactive epitopes within the individual *Borrelia* spp. protein antigens FlaB (GenBank Acc. No. ACI49679.1), DbpB (GenBank Acc. No. AAC70029.1), p66 (GenBank Acc. No. AAC66949.1), and OspC (GenBank Acc. No. ABQ42983.1) are described herein, and are believed, according to non-limiting theory, to find uses in the present compositions and methods as a consequence of the recognition by T cells of linear antigenic peptide epitopes.

An LD test based on this strategy is believed to provide at least two important benefits: First, activated T-cells proliferate more rapidly than antibody-producing B-cells, so the test may offer superior sensitivity to any antibody-detection test during the early stages of pathogenic *Borrelia* infection.

Secondly, the levels of antibodies produced in response to Lyme disease spirochetes typically remain elevated for months to years despite successful treatment, whereas regulation of T-cells typically manifests as moderation of T-cell activity levels following clearance of a provocative stimulus (e.g., infectious agent). Hence, the presently disclosed prognostic methods may offer superior assessment for whether a treatment course for LD has reduced (e.g., decreased in a statistically significant manner relative to an appropriate control) or eliminated a pathogenic *Borrelia* infection. These advantages are believed to arise because T-cells typically remain activated for only short periods of time following resolution of a *Borrelia* infection. Therefore, failure to detect an increased level of a T-cell immune response indicator (e.g., release of interferon-γ by activated T-cells) in response to a secondary in vitro challenge with the herein described composition, by T-cells that are present in a sample obtained from an LD subject after LD therapy, may also provide an accurate prediction of successful treatment.

As described herein, specific peptides based on clinically important individual *Borrelia* spp. (e.g., *B. garinii, B. burgdorferi, B. burgdorferi* B31) proteins contained within a multi-peptide cocktail were assessed for their ability, in a secondary in vitro immune response, to induce interferon-γ production (an exemplary T-cell immune response indicator) by activated T-cells obtained from LD patients. As proof of concept, the ability of such a cocktail comprised of *Borrelia* spp.-specific T-cell epitope-containing peptides to induce interferon-γ by Lyme disease-specific activated T-cells was specifically evaluated in blood samples from patients with early-stage *B. burgdorferi* infections. The levels of interferon-γ produced by T-cells collected from LD patients immediately prior to antibiotic therapy were also compared to the levels of interferon-γ produced by T-cells collected from LD patients approximately 60 days after the patients were treated effectively with antibiotics. BORRELIA T-CELL EPITOPE-CONTAINING PEPTIDES.

In certain embodiments the present disclosure provides a composition for diagnosis or prognosis of Lyme disease that is selected from a first composition and a second composition:

(I) the first composition comprising: (a) 1, 2, 3, 4, or 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 1, 2, 3, 4, 5, 6, 7, 8, 9, 10, 11, 12, or 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 1, 2, 3, 4, 5, 6, 7, 8, 9, 10, 11, 12, or 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 1 or 2 isolated OspC peptides that each comprise a *Borrelia* T-cell epitope and are selected from the OspC peptides having the amino acid sequences set forth in SEQ ID NO:32-33, or one or more variants thereof having at least 80% amino acid sequence identity to the amino acid sequences set forth in SEQ ID NOS:32-33, wherein the composition, after being contacted with whole blood obtained from a subject infected with a *Borrelia* species associated with Lyme disease, is capable of eliciting a secondary in vitro immune response by T-cells; and (II) the second composition comprising: (a) 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 2 isolated OspC peptides that each comprise a *Borrelia* T-cell epitope and are selected from the OspC peptides having the amino acid sequences set forth in SEQ ID NOS:32-33, or one or more variants thereof having at least 80% amino acid sequence identity to the amino acid sequences set forth in SEQ ID NOS:32-33.

A *Borrelia* spp. FlaB, DbpB, p66, or OspC peptide that comprises a *Borrelia* T-cell epitope for use in certain embodiments contemplated herein may comprise the amino acid sequence set forth for a FlaB peptide in any one of SEQ ID NOS:1-5, for a DbpB peptide in any one of SEQ ID NOS:6-18, for a p66 peptide in any one of SEQ ID NOS:19-31, and for an OspC peptide in any one of SEQ ID NOS:32-33, and may in certain other embodiments comprise a *Borrelia* T-cell epitope-containing peptide variant comprising a peptide having an amino acid sequence that is at least 80%, 81%, 82%, 83%, 84%, 85%, 86%, 87%, 88%, 89%, 90%, 91%, 92%, 93%, 94%, 95%, 96%, 97%, 98% or 99% identical to at least one of such peptides of SEQ ID NOS:1-33 and that is capable of being specifically recognized by a T-cell that is reactive with at least one pathogenic *Borrelia* species, preferably a *Borrelia* species that is pathogenic in humans, which pathogenic *Borrelia* species may include but need not be limited to *Borrelia burgdorferi, Borrelia burgdorferi* sensu stricto, *Borrelia azfelii, Borrelia garinii, Borrelia valaisiana, Borrelia spielmanii, Borrelia bissettii, Borrelia lusitaniae,* and *Borrelia bavariensis.*

*Borrelia* T-cell epitope-containing peptides of SEQ ID NOS:1-33 are set forth in Table 1.

TABLE 1

BORRELIA T-CELL EPITOPE-CONTAINING PEPTIDES:
BORRELIA SPP.-SPECIFIC REGIONS WITHIN FLAB, DBPB, P66, AND OSPC PROTEINS

| Antigen | peptide name/ (amino acid positions) | Sequence | SEQ ID NO: |
|---|---|---|---|
| Fla B | FlaB (51-75) | NVRTAEELGMQPAKINTPASLSGSQ | 1 |
|  | FlaB (66-85) | NTPASLSGSQASWTLRVHVG | 2 |
|  | FlaB (71-90) | LSGSQASWTLRVHVGANQDE | 3 |
|  | FlaB (88-107) | QDEAIAVNIYAANVANLFSG | 4 |
|  | FlaB (156-174) | SLAKIENAIRMISDQRANL | 5 |
| DbpB | DbpB (5-20) | SIVMVLFFDLLVACSIGLVE | 6 |
|  | DbpB (5-25) | LFFDLLVACSIGLVERTNAA | 7 |
|  | DbpB (16-40) | IGLVERTNAALESSSKDLKNKILKI | 8 |
|  | DbpB (31-55) | KDLKNKILKIKKEATGKGVLFEAFT | 9 |
|  | DbpB (46-70) | GKGVLFEAFTGLKTGSKVTSGGLAL | 10 |
|  | DbpB (61-85) | SKVTSGGLALREAKVQAIVETGKFL | 11 |
|  | DbpB (76-100) | QAIVETGKFLKIIEEEALKLKETGN | 12 |
|  | DbpB (91-115) | EALKLKETGNSGQFLAMFDLMLEVV | 13 |
|  | DbpB (106-130) | AMFDLMLEVVESLEDVGIIGLKARV | 14 |
|  | DbpB (121-145) | VGIIGLKARVLEESKNNPINTAERL | 15 |
|  | DbpB (136-160) | NNPINTAERLLAAKAQIENQLKVVK | 16 |
|  | DbpB (151-175) | QIENQLKVVKEKQNIENGGEKKNNK | 17 |
|  | DbpB (156-180) | LKVVKEKQNIENGGEKKNNKSKKKK | 18 |
| p66 | p66 (251-275) | FGLSGAYGNETFNNSSITYSLKDKS | 19 |
|  | p66 (266-290) | SITYSLKDKSVVGNDLLSPTLSNSA | 20 |
|  | p66 (281-305) | LLSPTLSNSAILASFGAKYKLGLTK | 21 |
|  | p66 (296-315) | GAKYKLGLTKINDKNTYLIL | 22 |
|  | p66 (301-320) | LGLTKINDKNTYLILQMGTD | 23 |
|  | p66 (311-330) | TYLILQMGTDFGIDPFASDF | 24 |
|  | p66 (316-335) | QMGTDFGIDPFASDFSIFGH | 25 |
|  | p66 (326-350) | FASDFSIFGHISKAANFKKETPSDP | 26 |
|  | p66 (341-365) | NFKKETPSDPNKKAEIFDPNGNALN | 27 |
|  | p66 (356-380) | IFDPNGNALNFSKNTELGIAFSTGA | 28 |
|  | p66 (371-390) | ELGIAFSTGASIGFAWNKDT | 29 |
|  | p66 (376-400) | FSTGASIGFAWNKDTGEKES | 30 |
|  | p66 (376-395) | FSTGASIGFAWNKDTGEKESWAIKG | 31 |
| OspC | OspC (171-185) | KEMLANSVKELTSPI | 32 |
|  | OspC (55-75) | ATKAIGKKIQQNGGLAVEAGH | 33 |

*Borrelia* T-cell epitope-containing peptide variants of a *Borrelia* T-cell epitope-containing peptide such as any of the peptides set forth as SEQ ID NOS:1-33 may contain one or more amino acid substitutions, additions, deletions, and/or insertions relative to the native *Borrelia* T-cell epitope-containing peptide sequence set forth in SEQ ID NOS:1-33 (e.g. wildtype, or predominant or naturally occurring allelic forms). Variants preferably exhibit at least about 80%, 81%, 82%, 83%, 84%, 85%, 86%, 87%, 88%, or 89% amino acid sequence identity and more preferably at least about 90%, 91%, 92%, 93%, 94%, 95%, 96%, 97%, 98% or 99% amino acid sequence identity to a corresponding portion of a native *Borrelia* spp. T-cell epitope-containing polypeptide sequence region, for example, the regions shown herein for the first time (Table 2) to contain T-cell epitopes from the *Borrelia* polypeptide antigens *Borrelia burgdorferi* FlaB (GenBank Acc. No. ACI49679.1), *Borrelia burgdorferi* DbpB (GenBank Acc. No. AAC70029.1), *Borrelia burgdorferi* p66 (GenBank Acc. No. AAC66949.1), and *Borrelia burgdorferi* OspC (GenBank Acc. No. ABQ42983.1). The percent identity may be readily determined by comparing sequences of the peptide variants with the corresponding portion of a full-length polypeptide, where corresponding portions can be readily identified according to established methods, for example, by aligning sequence regions that exhibit a high degree of sequence identity or sequence homology, optionally allowing for short sequence gaps as may arise due to insertions or deletions, or for conservative substitutions, or for short mismatched regions, or the like. Some techniques for sequence comparison include using computer algorithms well known to those having ordinary skill in the art, such as Align or the BLAST algorithm (Altschul, *J. Mol. Biol.* 219:555-565, 1991; Henikoff and Henikoff, *PNAS USA* 89:10915-10919, 1992), which is available at the NCBI website (see [online] Internet: <URL: http://www/ncbi.nlm.nih.gov/cgi-bin/BLAST). Default or custom parameters may be used.

Furthermore, computer algorithms are available in the art that enable the skilled artisan to predict the three-dimensional structure of a protein or peptide, in order to ascertain functional variants of a particular polypeptide. For instance, variants can be identified wherein all or a portion of the three-dimensional structure is not substantially altered by one or more modification, substitution, addition, deletion and/or insertion. (See, for example, Seemayer et al., 2014 *Bioinformat.* 30:3128; Raman et al., 2010 *ScienceExpress* 4 Feb. 2010 10.1126/science.1183649; Gribenko et al., 2009 *Proc. Nat. Acad. Sci. USA* 106:2601; Bradley et al., *Science* 309: 1868-1871 (2005); Schueler-Furman et al., *Science* 310:638 (2005); Dietz et al., *Proc. Nat. Acad. Sci. USA* 103:1244 (2006); Dodson et al., *Nature* 450:176 (2007); Qian et al., *Nature* 450:259 (2007); Baker, 2014 *Biochem. Soc. Trans.* 42:225; Correia et al., 2014 *Nature* 507:201; King et al., 2014 *Proc. Nat. Acad. Sci. USA* 111:8577; Roche et al., 2012 *PLoS One* 7(5):e38219; Zhang et al., 2013 *Meths. Enzymol.* 523:21; Khoury et al., 2014 *Trends Bio-* technol. 32:99; O'Meara et al., 2015 *J. Chem. Theory Comput.* 11:609; Park et al., 2015 *Structure* 23:1123; Bale et al., 2015 *Protein Sci.* doi:10.1002/pro.2748 Epub PMID 26174163; Park et al., 2015 Proteins doi: 10.1002/prot.24862 Epub PMID 26205421; Lin et al., 2015 *Proc. Nat. Acad. Sci. USA* pii:201509508 Epub PMID 26396255). In this way, one of skill in the art can readily determine whether a particular *Borrelia* T-cell epitope-containing peptide variant, or a functional fragment thereof, retains sufficient epitope structure so as to be capable of being specifically recognized by a T-cell that is reactive with at least one pathogenic *Borrelia* species.

A *Borrelia* T-cell epitope-containing peptide may be a peptide of at least 5, 6, 7, 8, 9, 10, 11, 12, 13, or 14 contiguous amino acids and in certain embodiments may typically be not more than 100, 95, 90, 85, 80, 75, 70, 65, 60, 55, or 50 amino acids in length. In certain preferred embodiments the *Borrelia* T-cell epitope-containing peptide may be a peptide of 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 contiguous amino acids in length.

It is understood that a T-cell epitope refers to a structural region of an antigen that can be specifically recognized by a T-cell receptor for antigen ("T-cell receptor"), typically in the context of an appropriate major histocompatibility complex (MHC) class I or class II molecule that presents the epitope to the T-cell receptor. T-cell epitope-containing peptides of about 8-13 amino acids in length are typically presented to CD8 T-cell receptors by class I MHC molecules; T-cell epitope-containing peptides of about 15-25 amino acids in length are typically presented to CD4 T-cell receptors by class II MHC molecules. T-cell receptors are not absolute in their specificity but are instead regarded as promiscuous; that is to say, a given T-cell receptor may be capable of specifically recognizing a particular T-cell epitope structure and also a range of closely related epitope structures. Specific recognition of an appropriately presented T-cell epitope by a T-cell may be detectable as stimulation of the generation of a T-cell immune response indicator such as those described herein (e.g., cytokine release by T-cells, such as IFN-γ release). Hence a *Borrelia* T-cell epitope-containing peptide may refer to a peptide antigen that is capable, in a secondary in vitro immune response, of stimulating a T-cell that has been primed (e.g., activated) to recognize a *Borrelia* spp. antigen, including situations where the *Borrelia* T-cell epitope-containing peptide is not identical to the *Borrelia* spp. antigen with which the T-cell may have been primed in vivo.

Methodologies for the design, production and testing of *Borrelia* T-cell epitope-containing peptides and variants functional fragments thereof as provided herein are all available by minor modification to existing knowledge in the art, for example, using conventional methods of virology, immunology, microbiology, molecular biology and recombinant DNA techniques, which are explained fully in the literature. See, e.g., Sambrook, et al. *Molecular Cloning: A Laboratory Manual* (2nd Edition, 1989); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984).

The terms "polypeptide", "protein" and "peptide" are used interchangeably and mean a polymer of amino acids not limited to any particular length. The term does not exclude modifications such as myristylation, sulfation, glycosylation, phosphorylation, formylation, and addition or deletion of signal sequences. The term "polypeptide" or "protein" means one or more chains of amino acids, wherein each chain comprises amino acids covalently linked by peptide bonds, and wherein said polypeptide or protein can comprise a plurality of chains non-covalently and/or covalently linked together by peptide bonds, having the sequence of native proteins, that is, proteins produced by naturally-occurring and specifically non-recombinant cells, or genetically-engineered or recombinant cells, and comprise molecules having the amino acid sequence of the native protein, or molecules having deletions from, additions to, and/or substitutions of one or more amino acids of the native sequence. Thus, a "polypeptide" or a "protein" can comprise one (termed "a monomer") or a plurality (termed "a multimer") of amino acid chains. The terms "peptide," "polypeptide" and "protein" specifically encompass the peptides of the present disclosure, or sequences that have deletions from, additions to, and/or substitutions of one or more amino acid of a herein described peptide.

The term "isolated" means that the material is removed from its original environment (e.g., the natural environment if it is naturally occurring). For example, a naturally occurring polypeptide or nucleic acid present in a living animal is not isolated, but the same polypeptide or nucleic acid, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide. The term "gene" means the segment of DNA involved in producing a polypeptide chain; it includes regions preceding and following the coding region "leader and trailer" as well as intervening sequences (introns) between individual coding segments (exons).

The terms "isolated protein", "isolated polypeptide" and "isolated peptide" referred to herein means that a subject protein, peptide or polypeptide (1) is free of at least some other proteins, peptides or polypeptides with which it would typically be found in nature, (2) is essentially free of other proteins, peptides or polypeptides from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein or polypeptide with which the isolated protein, isolated peptide or isolated polypeptide may be associated in nature, (6) is operably associated (by covalent or noncovalent interaction) with a polypeptide with which it is not associated in nature, or (7) does not occur in nature. Such an isolated protein, peptide or polypeptide can be encoded by genomic DNA, cDNA, mRNA or other RNA, or may be of synthetic origin according to any of a number of well known chemistries for artificial peptide and protein synthesis, or any combination thereof. In certain embodiments, the isolated protein, peptide or polypeptide is substantially free from proteins or polypeptides or other contaminants that are found in its natural environment that would interfere with its use (therapeutic, diagnostic, prophylactic, research or otherwise).

A "peptide fragment" or "polypeptide fragment" refers to a peptide or polypeptide, which can be monomeric or multimeric, that has an amino-terminal deletion, a carboxylterminal deletion, and/or an internal deletion or substitution of a naturally-occurring or recombinantly-produced polypeptide. As used herein, "contiguous amino acids" refers to covalently linked amino acids corresponding to an uninterrupted linear portion of a disclosed amino acid sequence. In certain embodiments, a polypeptide fragment can comprise an amino acid chain at least 5 to about 100 amino acids long. It will be appreciated that in certain embodiments, fragments are at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95 or 100 amino acids long.

Certain preferred embodiments contemplate wholly artificial chemical synthesis of the herein described peptides (e.g., a *Borrelia* T-cell epitope-containing peptide) according to any of a number of established methodologies, such as those described in *Amino Acid and Peptide Synthesis* (Jones, J., 2002 Oxford Univ. Press USA, New York), Ramakers et al. (2014 *Chem. Soc. Rev.* 43:2743), Verzele et al. (2013 *Chembiochem.* 14:1032), Chandrudu et al. (2013 *Molecules* 18:4373), and/or Mäde et al. (2004 *Beilstein J. Org. Chem.* 10:1197). For example, manual or preferably automated solid-phase peptide synthesis based on the Merrifield method or other solid-phase peptide synthetic techniques and subsequent improvements (e.g., Merrifield, 1963 *J. Am. Chem. Soc.* 85:2149; Mitchell et al., 1978 *J. Org. Chem.* 43:2485; Albericio, F. (2000). *Solid-Phase Synthesis: A Practical Guide* (1 ed.). Boca Raton: CRC Press; Nilsson et al., 2005 *Annu. Rev. Biophys. Biomol. Struct.* 34; Schnolzer et al., *Int. J. Peptide Res. Therap.* 13 (1-2): 31; Li et al. 2013 *Molecules* 18:9797) are routine in the peptide synthesis art and may be employed to chemically synthesize the herein described peptides.

A polypeptide or peptide may comprise a signal (or leader) sequence at the N-terminal end of the protein, which co-translationally or post-translationally directs transfer of the protein. The polypeptide or peptide may also be fused in-frame or conjugated to a linker or other sequence for ease of synthesis, purification or identification of the polypeptide (e.g., poly-His), or to enhance binding of the polypeptide or peptide to a solid support. Fusion domain polypeptides may be joined to the polypeptide or peptide at the N-terminus and/or at the C-terminus, and may include as non-limiting examples, immunoglobulin-derived sequences such as Ig constant region sequences or portions thereof, affinity tags such as His tag (e.g., hexahistidine or other polyhistidine), FLAG™ or myc or other peptide affinity tags, detectable polypeptide moieties such as green fluorescent protein (GFP) or variants thereof (e.g., yellow fluorescent protein (YFP), blue fluorescent protein (BFP), other aequorins or derivatives thereof, etc.) or other detectable polypeptide fusion domains, enzymes or portions thereof such as glutathione-S-transferase (GST) or other known enzymatic detection and/or reporter fusion domains, and the like, as will be familiar to the skilled artisan.

Systems for recombinant expression of peptides, polypeptides and proteins are known in the art and may in certain embodiments be used to produce the herein described peptides. For example, certain bacterial expression systems such as *E. coli* recombinant protein expression systems yield polypeptide products having N-terminal formylated methionine. In some situations a recombinantly produced peptide may therefore comprise an N-terminal methionine residue (which may be unmodified methionine or formylmethionine or another methionine analog, variant, mimetic or derivative as provided herein), sometimes referred to as initiator methionine, immediately preceding the desired peptide sequence (e.g., the *Borrelia* T-cell epitope-containing peptide). Thus also contemplated are embodiments in which one or more of the herein described *Borrelia* T-cell epitope-containing peptides are generated containing N-terminal methionine (e.g., as methionine or N-formylmethionine) and may be recombinantly expressed according to art-accepted practices in a host cell that also expresses methionine aminopeptidase (MAP), an enzyme that is capable of cleaving the N-terminal methionine to remove it from the nascent polypeptide product. See, e.g., Natarajan et al., 2011 *PLoS ONE* 6(5): e20176; Shen et al., 1993 *Proc. Natl. Acad. Sci. USA* 90:8108; Shen et al., 1997 *Prot. Eng.* 10:1085. Alternatively, the MAP enzyme itself may be produced recombinantly (e.g., Tsunasawa et al., 1997 *J. Biochem.* 122:843; Bradshaw et al., 1998 *Trends Bioch. Sci.* 23:263; Ben-Bassat et al., 1987 *J. Bacteriol.* 169:751) or obtained commercially (Sigma-Aldrich, St. Louis, Mo., e.g., catalog number M6435) and used to remove N-terminal methionine from the present peptides post-synthesis.

According to certain preferred embodiments a *Borrelia* T-cell epitope-containing peptide may comprise a peptide, polypeptide or peptidomimetic that includes, or that shares close sequence identity to or structural features with, a polypeptide of at least 5 and no more than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7 or 6 amino acids, comprising the amino acid sequence set forth in any one of SEQ ID NOS:1-33, wherein the peptide in which the *Borrelia* T-cell epitope is present is capable of being specifically recognized by a T-cell that is reactive with at least one pathogenic *Borrelia* species, preferably a *Borrelia* species that is pathogenic in humans, which pathogenic *Borrelia* species may include but need not be limited to *Borrelia burgdorferi*, *Borrelia burgdorferi* sensu stricto, *Borrelia azfelii*, *Borrelia garinii*, *Borrelia valaisiana*, *Borrelia spielmanii*, *Borrelia bissettii*, *Borrelia lusitaniae*, and *Borrelia bavariensis*. Assay methods for determining such T-cell reactivity are described herein and are also known generally in the art, except for the identities of *Borrelia* T-cell epitope-containing proteins and peptides which are disclosed herein for the first time.

As generally referred to in the art, and as used herein, sequence identity and sequence homology may be used interchangeably and generally refer to the percentage of nucleotides or amino acid residues in a candidate sequence that are identical with, respectively, the nucleotides or amino acid residues in a reference polynucleotide or polypeptide sequence, after aligning the sequences and introducing gaps, if necessary, to achieve the maximum percent sequence identity, and optionally not considering any conservative substitutions as part of the sequence identity. In certain embodiments, a variant of a peptide such as a herein disclosed *Borrelia* spp. T-cell epitope-containing peptide (e.g., a peptide according to one of SEQ ID NOS:1-33) shares at least about 80%, at least about 85%, at least about 90%, 91%, 92%, 93% or 94%, or at least about 95%, 96%, 97%, 98%, or 99% of the amino acid residues (or of the nucleotides in a polynucleotide encoding such a peptide) with the sequence of the peptide of any one of SEQ ID NOS:1-33. Such sequence identity may be determined according to well known sequence analysis algorithms, as also noted above, and including those available from the University of Wisconsin Genetics Computer Group (Madison, Wis.), such as FASTA, Gap, Bestfit, BLAST, or others.

"Natural or non-natural amino acid" includes any of the common naturally occurring amino acids which serve as building blocks for the biosynthesis of peptides, polypeptides and proteins (e.g., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), tyrosine (Y)) and also includes modified, derivatized, enantiomeric, rare and/or unusual amino acids, whether naturally occurring or synthetic, for instance, N-formylmethionine, hydroxyproline, hydroxylysine, desmosine, isodesmosine, ε-N-methyllysine, ε-N-trimethyllysine, methylhistidine, dehydrobutyrine, dehydroalanine, α-aminobutyric acid, β-alanine, γ-aminobutyric acid, homocysteine, homoserine, citrulline, ornithine and other amino acids that may be isolated from a natural source and/or that may be chemically synthesized, for instance, as may be found in *Proteins, Peptides and Amino Acids Sourcebook* (White, J. S. and White, D. C., 2002 Humana Press, Totowa, N.J.) or in *Amino Acid and Peptide Synthesis* (Jones, J., 2002 Oxford Univ. Press USA, New York) or in *Unnatural Amino Acids, ChemFiles Vol.* 1, No. 5 (2001 Fluka Chemie GmbH; Sigma-Aldrich, St. Louis, Mo.) or in *Unnatural Amino Acids II, ChemFiles Vol.* 2, No. 4 (2002 Fluka Chemie GmbH; Sigma-Aldrich, St. Louis, Mo.). Additional descriptions of natural and/or non-natural amino acids may be found, for example, in Kotha, 2003 *Acc. Chem. Res.* 36:342; Maruoka et al., 2004 *Proc. Nat. Acad. Sci. USA* 101:5824; Lundquist et al., 2001 *Org. Lett.* 3:781; Tang et al., 2002 *J. Org. Chem.* 67:7819; Rothman et al., 2003 *J. Org. Chem.* 68:6795; Krebs et al., 2004 *Chemistry* 10:544; Goodman et al., 2001 *Biopolymers* 60:229; Sabat et al., 2000 *Org. Left.* 2:1089; Fu et al., 2001 *J. Org. Chem.* 66:7118; and Hruby et al., 1994 *Meths. Mol. Biol.* 35:249. The standard three-letter abbreviations and one-letter symbols are used herein to designate natural and non-natural amino acids.

Other non-natural amino acids or amino acid analogues are known in the art and include, but are not limited to, non-natural L or D derivatives (such as D-amino acids present in peptides and/or peptidomimetics such as those presented above and elsewhere herein), fluorescent labeled amino acids, as well as specific examples including O-methyl-L-tyrosine, an L-3-(2-naphthyl)alanine, a 3-methyl-phenylalanine, 3-idio-tyrosine, O-propargyl-tyrosine, homoglutamine, an O-4-allyl-L-tyrosine, a 4-propyl-L-tyrosine, a 3-nitro-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-acetyl-L-phenylalanine, an m-acetyl-L-phenylalanine, selenomethionine, telluromethionine, selenocysteine, an alkyne phenylalanine, an O-allyl-L-tyrosine, an O-(2-propynyl)-L-tyrosine, a p-ethylthiocarbonyl-L-phenylalanine, a p-(3-oxobutanoyl)-L-phenylalanine, a p-benzoyl-L-phenylalanine, an L-phosphoserine, a phosphonoserine, a phosphonotyrosine, homopropargylglycine, azidohomoalanine, a p-iodo-phenylalanine, a p-bromo-L-phenylalanine, dihydroxy-phenylalanine, dihydroxyl-L-phenylalanine, a p-nitro-L-phenylalanine, an m-methoxy-L-phenylalanine, a p-iodo-phenylalanine, a p-bromophenylalanine, a p-amino-L-phenylalanine, and an isopropyl-L-phenylalanine, trifluoroleucine, norleucine ("Nle"), D-norleucine ("dNle" or "D-Nle"), 5-fluoro-tryptophan, para-halo-phenylalanine, homo-phenylalanine ("homo-Phe"), seleno-methionine, ethionine, S-nitroso-homocysteine, thia-proline, 3-thienylalanine, homo-allyl-glycine, trifluoroisoleucine, trans and cis-2-amino-4-hexenoic acid, 2-butynyl-glycine, allyl-glycine, para-azido-phenylalanine, para-cyano-phenylalanine, para-ethynyl-phenylalanine, hexafluoroleucine, 1,2,4-triazole-3-alanine, 2-fluoro-histidine, L-methyl histidine, 3-methyl-L-histidine, β-2-thienyl-L-alanine, β-(2-thiazolyl)-DL-alanine, homoproparglyglycine (HPG) and azidohomoalanine (AHA) and the like.

In certain embodiments a natural or non-natural amino acid may be present that comprises an aromatic side chain, as found, for example, in phenylalanine or tryptophan or analogues thereof including in other natural or non-natural amino acids based on the structures of which the skilled person will readily recognize when an aromatic ring system is present, typically in the form of an aromatic monocyclic or multicyclic hydrocarbon ring system consisting only of hydrogen and carbon and containing from 6 to 19 carbon atoms, where the ring system may be partially or fully saturated, and which may be present as a group that includes, but need not be limited to, groups such as fluorenyl, phenyl and naphthyl.

In certain embodiments a natural or non-natural amino acid may be present that comprises a hydrophobic side chain as found, for example, in alanine, valine, isoleucine, leucine, proline, phenylalanine, tryptophan or methionine or analogues thereof including in other natural or non-natural amino acids based on the structures of which the skilled person will readily recognize when a hydrophobic side chain (e.g., typically one that is non-polar when in a physiological milieu) is present. In certain embodiments a natural or non-natural amino acid may be present that comprises a basic side chain as found, for example, in lysine, arginine or histidine or analogues thereof including in other natural or non-natural amino acids based on the structures of which the skilled person will readily recognize when a basic (e.g., typically polar and having a positive charge when in a physiological milieu) is present.

Peptides disclosed herein may in certain embodiments include L- and/or D-amino acids so long as the biological activity of the peptide is maintained (e.g., the *Borrelia* spp. T-cell epitope-containing peptide is capable of being recognized in a secondary in vitro immune response by T-cells from a subject infected with a *Borrelia* species that is associated with Lyme disease, as evidenced by stimulation of the generation of a T-cell immune response indicator as described herein). The peptides also may comprise in certain embodiments any of a variety of known natural and artificial post-translational or post-synthetic covalent chemical modifications by reactions that may include glycosylation (e.g., N-linked oligosaccharide addition at asparagine residues, O-linked oligosaccharide addition at serine or threonine residues, glycation, or the like), fatty acylation, acetylation, formylation, PEGylation, and phosphorylation. Peptides herein disclosed may further include analogs, alleles and allelic variants which may contain amino acid deletions, or additions or substitutions of one or more amino acid residues with other naturally occurring amino acid residues or non-natural amino acid residues.

Peptide and non-peptide analogs may be referred to as peptide mimetics or peptidomimetics, and are known in the pharmaceutical industry (Fauchere, *J. Adv. Drug Res.* 15:29 (1986); Evans et al. *J. Med. Chem.* 30: 1229 (1987)). These compounds may contain one or more non-natural amino acid residue(s), one or more chemical modification moieties (for example, glycosylation, pegylation, fluorescence, radioactivity, or other moiety), and/or one or more non-natural peptide bond(s) (for example, a reduced peptide bond: —$CH_2$—$NH_2$—). Peptidomimetics may be developed by a variety of methods, including by computerized molecular modeling, random or site-directed mutagenesis, PCR-based strategies, chemical mutagenesis, and others.

As also described above, certain embodiments also relate to peptidomimetics, or "artificial" polypeptides. Such polypeptides may contain one or more amino acid insertions, deletions or substitutions, one or more altered or artificial peptide bond, one or more chemical moiety (such as polyethylene glycol, glycosylation, a detectable label, or other moiety), and/or one or more non-natural amino acid. Synthesis of peptidomimetics is well known in the art and may include altering naturally occurring proteins or polypeptides by chemical mutagenesis, single or multi-site-directed mutagenesis, PCR shuffling, use of altered aminoacyl tRNA or aminoacyl tRNA synthetase molecules, the use of "stop" codons such as amber suppressors, the use of four or five base-pair codons, or other means.

Table 2 shows *Borrelia* spp. sources, the identities of the source proteins, and the amino acid sequence regions from which all or portions of the *Borrelia* spp. T-cell epitope-containing peptides of SEQ ID NOS:1-33 (shown in Table 3) are obtained or derived.

TABLE 2

Amino acid sequences of *Borrelia* spp.-specific peptide regions within FlaB, DbpB, p66, and OspC proteins

| Source protein | Source species | GenBank Acc. No. | Amino Acid Position Nos. | Amino Acid Sequence | SEQ ID NO: |
|---|---|---|---|---|---|
| FlaB | *Borrelia burgdorferi* | ACI49679.1 | 51-90 | NVRTAEELGMQPAKI NTPASLSGSQASWTL RVHVGANQDE | 34 |
| FlaB | *Borrelia burgdorferi* | ACI49679.1 | 88-107 | QDEAIAVNIYAANVA NLFSG | 35 |
| FlaB | *Borrelia burgdorferi* | ACI49679.1 | 156-174 | SLAKIENAIRMISDQ RANL | 36 |
| DbpB | *Borrelia burgdorferi* | AAC70029.1 | 1-180 | SIVMVLFFDLLVACS IGLVERTNAALESSS KDLKNKILKIKKEAT GKGVLFEAFTGLKTG SKVTSGGLALREAKV QAIVETGKFLKIIEE EALKLKETGNSGQFL AMFDLMLEVVESLED VGIIGLKARVLEESK NNPINTAERLLAAKA QIENQLKVVKEKQNI ENGGEKKNNKSKKKK | 37 |
| p66 | *Borrelia burgdorferi* B31 | AAC66949.1 | 251-400 | FGLSGAYGNE TFNNSSITYS LKDKSVVGND LLSPTLSNSA ILASFGAKYK LGLTKINDKN TYLILQMGTD FGIDPFASDF SIFGHISKAA NFKKETPSDP NKKAEIFDPN GNALNFSKNT ELGIAFSTGA SIGFAWNKDT GEKESWAIKG | 38 |
| OspC | *Borrelia burgdorferi* | ABQ42983.1 | 55-75 | ATKAIGKKIQQNGGLA VEAGH | 39 |
| OspC | *Borrelia burgdorferi* | ABQ42983.1 | 171-185 | KEMLANSVKELTSPI | 40 |

TABLE 3

Synthetic peptides prepared from *Borrelia* spp.-specific regions within FlaB, DbpB, p66, and OspC proteins

| Antigen pool 1 µg each/mL | peptide name/ position | Sequence | SEQ ID NO: |
|---|---|---|---|
| Fla B | FlaB (51-75) | NVRTAEELGMQPAKINTPASLSGS Q | 1 |

TABLE 3-continued

Synthetic peptides prepared from *Borrelia* spp.-specific regions within FlaB, DbpB, p66, and OspC proteins

| Antigen pool 1 µg each/mL | peptide name/ position | Sequence | SEQ ID NO: |
|---|---|---|---|
| | FlaB (66-85) | NTPASLSGSQASWTLRVHVG | 2 |
| | FlaB (71-90) | LSGSQASWTLRVHVGANQDE | 3 |
| | FlaB (88-107) | QDEAIAVNIYAANVANLFSG | 4 |
| | FlaB (156-174) | SLAKIENAIRMISDQRANL | 5 |
| DbpB | DbpB (5-20) | SIVMVLFFDLLVACSIGLVE | 6 |
| | DbpB (5-25) | LFFDLLVACSIGLVERTNAA | 7 |
| | DbpB (16-40) | IGLVERTNAALESSSKDLKNKILKI | 8 |
| | DbpB (31-55) | KDLKNKILKIKKEATGKGVLFEAFT | 9 |
| | DbpB (46-70) | GKGVLFEAFTGLKTGSKVTSGGLAL | 10 |
| | DbpB (61-85) | SKVTSGGLALREAKVQAIVETGKFL | 11 |
| | DbpB (76-100) | QAIVETGKFLKIIEEEALKLKETGN | 12 |
| | DbpB (91-115) | EALKLKETGNSGQFLAMFDLMLEVV | 13 |
| | DbpB (106-130) | AMFDLMLEVVESLEDVGIIGLKARV | 14 |
| | DbpB (121-145) | VGIIGLKARVLEESKNNPINTAERL | 15 |
| | DbpB (136-160) | NNPINTAERLLAAKAQIENQLKVVK | 16 |
| | DbpB (151-175) | QIENQLKVVKEKQNIENGGEKKNNK | 17 |
| | DbpB (156-180) | LKVVKEKQNIENGGEKKNNKSKKKK | 18 |
| p66 | p66 (251-275) | FGLSGAYGNETFNNSSITYSLKDKS | 19 |
| | p66 (266-290) | SITYSLKDKSVVGNDLLSPTLSNSA | 20 |
| | p66 (281-305) | LLSPTLSNSAILASFGAKYKLGLTK | 21 |
| | p66 (296-315) | GAKYKLGLTKINDKNTYLIL | 22 |
| | p66 (301-320) | LGLTKINDKNTYLILQMGTD | 23 |
| | p66 (311-330) | TYLILQMGTDFGIDPFASDF | 24 |
| | p66 (316-335) | QMGTDFGIDPFASDFSIFGH | 25 |
| | p66 (326-350) | FASDFSIFGHISKAANFKKETPSDP | 26 |
| | p66 (341-365) | NFKKETPSDPNKKAEIFDPNGNALN | 27 |
| | p66 (356-380) | IFDPNGNALNFSKNTELGIAFSTGA | 28 |
| | p66 (371-390) | ELGIAFSTGASIGFAWNKDT | 29 |
| | p66 (376-400) | FSTGASIGFAWNKDTGEKES | 30 |
| | p66 (376-395) | FSTGASIGFAWNKDTGEKESWAIKG | 31 |
| OspC | OspC (171-185) | KEMLANSVKELTSPI | 32 |
| | OspC (55-75) | ATKAIGKKIQQNGGLAVEAGH | 33 |

Any combination of the peptides of Table 3 may be employed in certain presently contemplated embodiments of the herein disclosed compositions, and in particularly preferred embodiments at least one peptide is present from each of the four disclosed *Borrelia* polypeptide regions, FlaB, DbpB, p66 and OspC: FlaB [SEQ ID NOS:1-5], DbpB [SEQ ID NOS:6-18], p66 [SEQ ID NOS:19-31] and OspC [SEQ ID NOS:32-33]. The amounts of the several peptides relative to one another, and the absolute amounts of one or more of said peptides, may be varied according to the assay design and particular technique in which the composition is to be used, as will be familiar to the skilled artisan according to particular immunochemical, immunological and/or biochemical methodologies. By way of illustration and not limitation, in certain embodiments the composition may comprise at least about one nanogram of each peptide and not more than about 100 nanograms of each peptide; in certain embodiments the composition may comprise at least about 100, 200, 300, or 400 nanograms and not more than about 500 nanograms of each peptide; in certain embodiments the composition may comprise at least about 500, 600, 700, 800, or 900 nanograms and not more than about 1000 nanograms of each peptide; in certain embodiments the composition may comprise at least about 1.0, 1.1, 1.2, 1.3, 1.4, 1.5, 1.6, 1.7, 1.8, or 1.9 micrograms and not more than about 2 micrograms of each peptide, and in certain embodiments the composition may comprise at least about 1, 2, 3, 4, 5, 6, 7, 8, or 9 micrograms and not more than about 10 micrograms of each peptide.

Methods for Diagnosis or Prognosis of Lyme Disease

As disclosed herein there are provided, in certain embodiments, compositions and methods for detecting Lyme disease in a subject, or for monitoring the efficacy of a treatment for Lyme disease in a subject, based in part on the discovery that a peptide cocktail containing at least one *Borrelia*-specific T-cell epitope-containing peptide from each of the presently identified *Borrelia* spp. FlaB, DbpB, p66 and OspC protein regions (e.g., Tables 2 and 3) provides a composition with which T-cells from substantially all LD patients will react in a secondary in vitro immune response, by generating a T-cell immune response indicator (e.g., interferon-γ release) as provided herein.

These and related embodiments thus permit detection of LD in a subject at a point in time that is earlier in the progression of disease than the time at which the appearance of *Borrelia*-specific antibodies can be detected in the subject. Additionally, and as also noted above, the present disclosure permits assessment of the efficacy of a treatment for LD based on a decline in detectable *Borrelia*-specific T-cell responsiveness by circulating T-cells obtained from a subject who has undergone successful LD treatment to eradicate *Borrelia* spirochetes, in contrast to an assessment of detectable *Borrelia*-specific antibodies, which can remain in the circulation at high levels for many months or even years following successful LD treatment and thus would mask the effects of successful eradication of *Borrelia* spirochetes.

Accordingly and in certain embodiments there is provided a method for detecting Lyme disease in a subject, or for monitoring efficacy of a treatment for Lyme disease in a subject, comprising (A) contacting in vitro (i) a first biological sample obtained at a first timepoint a subject known to have or suspected of being at risk for having Lyme disease, wherein the biological sample comprises T-cells and antigen-presenting cells, and (ii) a peptide composition for diagnosis or prognosis of Lyme disease, to obtain a first test incubation mixture; (B) incubating the first test incubation mixture under conditions and for a time sufficient for specific recognition by said T-cells of a *Borrelia* T-cell epitope that is present in said peptide composition to stimulate generation of a T-cell immune response indicator; and (C) detecting a first level of the T-cell immune response indicator in the first test incubation mixture, wherein presence of a *Borrelia* infection in the subject is indicated by detection in (C) of said first level of the T-cell immune response indicator that is increased relative to a first control level of the T-cell immune response indicator obtained by incubating the first biological sample in a first control incubation without the peptide composition for diagnosis or prognosis of Lyme disease, and wherein the peptide composition for diagnosis or prognosis of Lyme disease comprises a peptide cocktail containing at least one *Borrelia*-specific T-cell epitope-containing peptide from each of the presently identified *Borrelia* spp. FlaB, DbpB, p66 and OspC protein regions (e.g., Tables 2 and 3), for example:

(a) 1, 2, 3, 4, or 5 isolated FlaB peptides that each comprise a *Borrelia* T-cell epitope and are selected from the FlaB peptides having the amino acid sequences set forth in SEQ ID NOS:1-5, or one or more variants thereof having at least 80% amino acid sequence identity to the amino acid sequences set forth in SEQ ID NOS:1-5; (b) 1, 2, 3, 4, 5, 6, 7, 8, 9, 10, 11, 12, or 13 isolated DbpB peptides that each comprise a *Borrelia* T-cell epitope and are selected from the DbpB peptides having the amino acid sequences set forth in SEQ ID NOS:6-18, or one or more variants thereof having at least 80% amino acid sequence identity to the amino acid sequences set forth in SEQ ID NOS:6-18; (c) 1, 2, 3, 4, 5, 6, 7, 8, 9, 10, 11, 12, or 13 isolated p66 peptides that each comprise a *Borrelia* T-cell epitope and are selected from the p66 peptides having the amino acid sequences set forth in SEQ ID NOS:19-31, or one or more variants thereof having at least 80% amino acid sequence identity to the amino acid sequences set forth in SEQ ID NOS:19-31; and (d) 1 or 2 isolated OspC peptides that each comprise a *Borrelia* T-cell epitope and are selected from the OspC peptides having the amino acid sequences set forth in SEQ ID NO:32-33, or one or more variants thereof having at least 80% amino acid sequence identity to the amino acid sequences set forth in SEQ ID NOS:32-33, and thereby detecting Lyme disease in the subject, or monitoring efficacy of the treatment for Lyme disease in the subject.

In certain preferred embodiments, the first timepoint is prior to administration to the subject of treatment for Lyme disease.

In certain further embodiments the method further comprises (D) contacting in vitro (i) a second biological sample obtained from the subject at a second timepoint that is later than the first timepoint and is after administration to the subject of treatment for Lyme disease, wherein the second biological sample comprises T-cells and antigen-presenting cells, and (ii) the peptide composition for diagnosis or prognosis of Lyme disease, to obtain a second test incubation mixture; (E) incubating the second test incubation mixture under conditions and for a time sufficient for specific recognition by said T-cells of a *Borrelia* T-cell epitope that is present in said peptide composition to stimulate generation of a T-cell immune response indicator; and (F) detecting a second level of the T-cell immune response indicator in the second test incubation mixture, wherein presence of a *Borrelia* infection in the subject is indicated by detection in (F) of said second level of the T-cell immune response indicator that is increased relative to a second control level of the T-cell immune response indicator obtained by incubating the second biological sample in a second control incubation without the peptide composition for diagnosis or prognosis of Lyme disease, and wherein efficacy of the treatment for Lyme disease is indicated by detection in (F) of said second level of the T-cell immune response indicator that is decreased relative to the first level of the T-cell immune response indicator that is detected in (C).

In these and certain related embodiments, it will therefore be recognized that the first timepoint is prior to administration to the subject of a given treatment for Lyme disease, whilst the second or subsequent timepoints may be after administration to the subject of the given treatment for LD, such that efficacy of the treatment may be determined, as reflected, for example, by a decrease (e.g., a statistically significant reduction relative to an appropriate control) in the second level of the T-cell immune response indicator that is detected. By way of non-limiting theory, such a result would signify that at the second or subsequent timepoint, the second biological sample contains lower levels of *Borrelia*-specific T-cell reactivity when assayed for stimulation of generation of a T-cell immune response indicator relative to the first timepoint, as a consequence of negatively-regulated and/or absent T-cell reactivity in the second sample due to substantial clearance of the *Borrelia* infection in the subject following the LD treatment.

In this manner it will be appreciated that the severity of a *Borrelia* infection associated with LD may be monitored over various time periods, such as over the course of one or a plurality of second timepoints, to assess disease progression as reflected by T-cell immune response indicator level as an apparent indicator of *Borrelia* bacterial load in the subject, and also to assess the efficacy of one or more treatments for LD. It may in certain cases be desirable to repeatedly test a plurality of biological samples obtained from a subject over a succession of second and subsequent timepoints in order to monitor the *Borrelia*-specific T-cell activity in the subject. Accordingly, in certain embodiments the presently described steps of contacting, incubating, and detecting may be repeated any number of times in situations where it may be desirable to monitor LD in a subject over an extended time period, for example over a plurality of second timepoints such as 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more second timepoints, which may be separated from one another by variable intervals that may be intervals of several days, weeks, months, or years.

Certain embodiments described herein thus contemplate compositions and/or methods that relate to one or more antibiotic compound known to the art as being appropriate for use in the treatment of Lyme disease, for instance, based on the antibiotic having an effective activity profile against a pathogenic *Borrelia* species such as any of the *Borrelia* spp. referred to herein, and especially with respect to human pathogenic *Borrelia* spp. As understood by a person skilled in the medical art, the terms, "treat" and "treatment," refer to medical management of a disease, disorder, or condition of a subject (i.e., patient, host, who may be a human or non-human animal) (see, e.g., Stedman's Medical Dictionary).

Antibiotics are known in the art and typically comprise a drug made from a compound produced by one species of microorganism to kill another species of microorganism, or a synthetic product having an identical or similar chemical structure and mechanism of action, e.g., a drug that destroys microorganisms within or on the body of a living organism, including such drug when applied topically.

Antibiotics that are known to the art as appropriate for treatment of Lyme disease may include, but need not be limited to, one or more of tetracyclines; oxytetracycline, tetracycline, doxycycline, or minocycline; penicillins; amoxicillin or penicillin; cephalosporins; cefaclor, cefbuperazone, cefminox, cefotaxime, cefotetan, cefmetazole, cefoxitin, cefuroxime axetil, cefuroxime acetyl, ceftin, or ceftriaxone; macrolides; azithromycin, clarithromycin, or erythromycin (see, e.g., Cameron et al., 2014 *Expert Rev Anti Infect Ther.* 12(9): 1103-1135; Shapiro, 2014 *N. Engl. J. Med.* 370(18):1724-31; Wright et al., 2012 *Am. Fam. Physician* 85:1086). Compendia of these and other clinically useful antibiotics are available and known to those familiar with the art (e.g., Washington University School of Medicine, *The Washington Manual of Medical Therapeutics* (32$^{nd}$ Ed.), 2007 Lippincott, Williams and Wilkins, Philadelphia, Pa.; Hauser, A L, *Antibiotic Basics for Clinicians,* 2007 Lippincott, Williams and Wilkins, Philadelphia, Pa.).

For use in the methods described herein, a biological sample may be obtained from a subject for determining the presence and level of a T-cell immune response indicator as presently disclosed. A suitable biological sample may comprise, for instance, a whole blood sample, or a cerebrospinal fluid sample, or a synovial fluid sample, any of which may be obtained from a subject (e.g., a human or animal subject and, in preferred embodiments, a human) having or suspected of being at risk for having Lyme disease, such as a patient who has sustained a tick bite or who presents clinically with erythema migrans or who otherwise may have one or more Lyme disease risk factors, as will be recognized by those skilled in the art (see, e.g., Shapiro, 2014 *N. Engl. J. Med.* 370:1724; Wright et al., 2012 *Am. Fam. Physician* 85:1086). In certain embodiments the biological sample may comprise at least one of whole blood (optionally with an anticoagulant), or a cellular fraction of whole blood, or isolated peripheral blood white cells, or isolated peripheral blood mononuclear cells. Biological samples may be obtained from a subject at a first timepoint that is prior to administration to the subject of an LD treatment, which biological sample may be useful diagnostically and/or as a control for establishing baseline (i.e., pre-therapeutic) data; additional biological samples may be obtained from the subject at one or a plurality of second timepoints that are after administration to the subject of the LD treatment.

Detection of T-Cell Immune Response Indicators

In vitro antigen-specific T-cell responses are typically determined by comparisons of observed T-cell responses according to any of a number of described measurable T-cell functional parameters (e.g., proliferation, cytokine expression, cytokine biosynthesis, cytokine release, altered cell surface marker phenotype, etc.) that may be made between T-cells that are exposed to a cognate antigen in an appropriate context (e.g., the antigen used to prime or activate the T-cells, when presented by immunocompatible antigen-presenting cells) and T-cells from the same source population that are exposed instead to a structurally distinct or irrelevant control antigen. A response to the cognate antigen that is greater, with statistical significance, than the response to the control antigen signifies antigen-specificity.

The level of a secondary in vitro *Borrelia* spp.-specific immune response may be determined by any one of numerous immunological methods described herein and/or routinely practiced in the art. The level of the secondary in vitro *Borrelia* spp.-specific immune response may be determined at one or a plurality of timepoints, including timepoints that are prior to and following administration to the subject from whom the biological sample comprising T-cells and antigen-presenting cells are obtained (e.g., a subject known to have or suspected of having Lyme disease) of any one or more of the herein described treatments for Lyme disease (e.g., one or more antibiotics).

As described in the Examples, the presently disclosed composition for diagnosis or prognosis comprising *Borrelia* spp. T-cell epitope-containing peptides (e.g., one or more FlaB, DbpB, p66, and OspC peptides of SEQ ID NOS:1-33 or variants thereof as disclosed herein) was shown to be capable of stimulating detectable generation of a T-cell immune response indicator in a test incubation in vitro by a biological sample comprising T-cells and antigen-presenting cells from a subject with an early stage infection by a *Borrelia* species associated with Lyme disease. The level of the T-cell immune response indicator that was detected was increased relative to a control level of the indicator that was obtained by incubating the biological sample in a control incubation that was otherwise identical to the test incubation except the *Borrelia* spp. peptide composition was omitted.

An increased level of a T-cell immune response indicator as provided herein thus may, in certain embodiments, take the form of a statistically significant increase in the level of the indicator that is detectable following incubation of T-cells and antigen presenting cells with the herein described *Borrelia* T-cell epitope-containing peptide composition (FlaB, DbpB, p66, OspC) under conditions and for a time sufficient for specific antigen recognition by the T-cells, relative to the level of the indicator that is detectable under appropriate control conditions (e.g., without the *Borrelia* peptide composition present).

By way of illustration and not limitation, in preferred embodiments, the T-cell immune response indicator that is generated by stimulation of T-cells with the *Borrelia* T-cell epitope-containing peptide composition is at least one T-cell cytokine that is induced, expressed and/or released by the T-cells following incubation in vitro. Preferably the T-cell cytokine is selected from IL-1α, IL-1β, IL-2, IL-10, IL-12, IL-17, TNF-α, TNF-β, and IFN-γ. In certain preferred embodiments, released IFN-γ is the T-cell immune response indicator that is generated by stimulation of T-cells with the *Borrelia* T-cell epitope-containing peptide composition. The contemplated embodiments are not, however, intended to be so limited, and therefore may include any of a wide variety of methodologies for assessing a biological sample as provided herein for its ability to mount a secondary in vitro antigen-specific response to the herein described *Borrelia* T-cell epitope-containing peptide composition. Various assay configurations and techniques are known in the art (e.g., *Current Protocols in Immunology*, John Wiley & Sons, New York, N.Y. (2009)) and may be adapted to the present methods based on the instant disclosure. Levels of cytokines thus may be determined according to methods described herein and practiced in the art, including for example, ELISA, ELISPOT, intracellular cytokine staining, and/or flow cytometry.

In a preferred embodiment the T-cell immune response indicator is IFN-γ released by T-cells of the biological sample during the step of incubating the sample with the herein described *Borrelia* T-cell epitope-containing peptide composition, and the level of released IFN-γ is determined immunochemically using any of a number of in vitro techniques by which IFN-γ is detected by determining detectable specific binding of a binding agent to the T-cell cytokine (i.e., IFN-γ). The binding agent may thus comprise at least one antibody that binds specifically to the cytokine (e.g., IFN-γ), which antibody may comprise at least one monoclonal antibody or which may instead comprise a polyclonal antibody. According to certain embodiments the T-cell immune response indicator is a cytokine that is released by T-cells and is detected by binding to an antibody that is immobilized on a solid phase.

An exemplary immunometric assay for IFN-γ is the QUANTIFERON® assay (available from Cellestis, Ltd., Carnegie, Victoria, Australia), which is established as a gold standard for IFN-γ determination in a widely used test for tuberculosis (e.g., Pai et al., 2004 *Lancet Infect Dis* 4:761) and from which the quantitative detection of IFN-γ can be adapted for use with the herein described *Borrelia* antigens instead of with tuberculosis antigens. (See also, e.g., Yun et al., 2014 *J. Clin. Microbiol.* 52:90; Belknap et al., 2014 *Clin. Lab. Med.* 34:337; Ferguson et al., 2015 *Transplantation* 99:1084; Ruan et al. 2014 *Clin. Rheumatol.* Epub PMID 25376466.)

A binding partner or an antibody is said to be "immunospecific," "specific for" or to "specifically bind" an antigen of interest (e.g., a cytokine that is being assayed as a detectable T-cell immune response indicator, for instance, IFN-γ) if the antibody reacts at a detectable level with the antigen, preferably with an affinity constant, $K_a$, of greater than or equal to about $10^4$ $M^{-1}$, or greater than or equal to about $10^5$ $M^{-1}$, greater than or equal to about $10^6$ $M^{-1}$, greater than or equal to about $10^7$ $M^{-1}$, or greater than or equal to $10^8$ $M^{-1}$. Affinity of an antibody for its cognate antigen is also commonly expressed as a dissociation constant $K_D$, and an antibody specifically binds to the antigen of interest if it binds with a $K_D$ of less than or equal to $10^{-4}$ M, less than or equal to about $10^{-5}$ M, less than or equal to about $10^{-6}$ M, less than or equal to $10^{-7}$ M, or less than or equal to $10^{-8}$ M.

Affinities of binding partners or antibodies can be readily determined using conventional techniques, for example, those described by Scatchard et al. (*Ann. N.Y. Acad. Sci. USA* 51:660 (1949)) and by surface plasmon resonance (SPR; BIAcore™, Biosensor, Piscataway, N.J.). For surface plasmon resonance, target molecules are immobilized on a solid phase and exposed to a binding partner (or ligand) in a mobile phase running along a flow cell. If ligand binding to the immobilized target occurs, the local refractive index changes, leading to a change in SPR angle, which can be monitored in real time by detecting changes in the intensity of the reflected light. The rates of change of the SPR signal can be analyzed to yield apparent rate constants for the association and dissociation phases of the binding reaction. The ratio of these values gives the apparent equilibrium constant (affinity) (see, e.g., Wolff et al., *Cancer Res.* 53:2560-2565 (1993)).

As used herein, the term "polyclonal antibody" refers to an antibody obtained from a population of antigen-specific antibodies that recognize more than one epitope of the specific antigen. "Antigen" or "immunogen" refers to a peptide, lipid, polysaccharide or polynucleotide which is recognized by the adaptive immune system. Antigens may be self or non-self molecules. Examples of antigens include, but are not limited to, bacterial cell wall components, pollen, and rh factor. The region of an antigen that is specifically recognized by a specific antibody, or by a specific T-cell receptor, is an "epitope" or "antigenic determinant." A single antigen may have multiple epitopes.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different epitopes, each monoclonal antibody is directed against a single epitope of the antigen. In addition to their specificity, the monoclonal antibodies are advantageous in that they may be synthesized uncontaminated by other antibodies. The modifier "monoclonal" is not to be construed as requiring production of the antibody by any particular method. For example, monoclonal antibodies may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). The "monoclonal antibodies" may also be isolated from phage antibody libraries using the techniques described in Clackson et al., *Nature*, 352:624-628 (1991) and Marks et al., *J. Mol. Biol.*, 222:581-597 (1991), for example.

Nucleic Acids and Polynucleotides

*Borrelia* spp. T-cell epitope-containing polypeptides and peptides as provided herein, and encoding nucleic acid molecules and vectors, may be isolated and/or purified, e.g. from their natural environment, in substantially pure or homogeneous form, or, in the case of nucleic acid, free or substantially free of nucleic acid or genes of origin other than the sequence encoding a polypeptide with the desired function. Nucleic acid may comprise DNA or RNA and may be wholly or partially synthetic. Reference to a nucleotide sequence as set out herein encompasses a DNA molecule with the specified sequence, and encompasses a RNA molecule with the specified sequence in which U is substituted for T, unless context requires otherwise.

The present invention thus further provides in certain embodiments an isolated nucleic acid encoding any of the *Borrelia* spp. T-cell epitope-containing peptides having the amino acid sequences set forth in SEQ ID NOS:1-33.

The term "operably linked" means that the components to which the term is applied are in a relationship that allows them to carry out their inherent functions under suitable conditions. For example, a transcription control sequence "operably linked" to a protein coding sequence is ligated thereto so that expression of the protein coding sequence is achieved under conditions compatible with the transcriptional activity of the control sequences.

The term "control sequence" as used herein refers to polynucleotide sequences that can affect expression, processing or intracellular localization of coding sequences to which they are ligated or operably linked. The nature of such control sequences may depend upon the host organism. In particular embodiments, transcription control sequences for prokaryotes may include a promoter, ribosomal binding site, and transcription termination sequence. In other particular embodiments, transcription control sequences for eukaryotes may include promoters comprising one or a plurality of recognition sites for transcription factors, transcription enhancer sequences, transcription termination sequences and polyadenylation sequences. In certain embodiments, "control sequences" can include leader sequences and/or fusion partner sequences.

The term "polynucleotide" as referred to herein means single-stranded or double-stranded nucleic acid polymers. In certain embodiments, the nucleotides comprising the polynucleotide can be ribonucleotides or deoxyribonucleotides or a modified form of either type of nucleotide. Such modifications may include base modifications such as bromouridine, ribose modifications such as arabinoside and 2',3'-dideoxyribose and internucleotide linkage modifications such as phosphorothioate, phosphorodithioate, phosphoroselenoate, phosphorodiselenoate, phosphoroanilothioate, phoshoraniladate and phosphoroamidate. The term "polynucleotide" specifically includes single and double stranded forms of DNA.

The term "naturally occurring nucleotides" includes deoxyribonucleotides and ribonucleotides. The term "modified nucleotides" includes nucleotides with modified or substituted sugar groups and the like. The term "oligonucleotide linkages" includes oligonucleotide linkages such as phosphorothioate, phosphorodithioate, phosphoroselenoate, phosphorodiselenoate, phosphoroanilothioate, phoshoraniladate, phosphoroamidate, and the like. See, e.g., LaPlanche et al., 1986, *Nucl. Acids Res.*, 14:9081; Stec et al., 1984, *J. Am. Chem. Soc.*, 106:6077; Stein et al., 1988, *Nucl. Acids Res.*, 16:3209; Zon et al., 1991, *Anti-Cancer Drug Design*, 6:539; Zon et al., 1991, *Olignonucleotdies and Analogues: A Practical Approach*, pp. 87-108 (F. Eckstein, Ed.), Oxford University Press, Oxford England; Stec et al., U.S. Pat. No. 5,151,510; Uhlmann and Peyman, 1990, *Chemical Reviews*, 90:543, the disclosures of which are hereby incorporated by reference for any purpose. An oligonucleotide can include a detectable label to enable detection of the oligonucleotide or hybridization thereof.

The term "vector" is used to refer to any molecule (e.g., nucleic acid, plasmid, or virus) used to transfer coding information to a host cell. The term "expression vector" refers to a vector that is suitable for transformation of a host cell and contains nucleic acid sequences that direct and/or control expression of inserted heterologous nucleic acid sequences. Expression includes, but is not limited to, processes such as transcription, translation, and RNA splicing, if introns are present.

As will be understood by those skilled in the art, polynucleotides may include genomic sequences, extra-genomic and plasmid-encoded sequences and smaller engineered gene segments that express, or may be adapted to express, proteins, polypeptides, peptides and the like. Such segments may be naturally isolated, or modified synthetically by the skilled person.

As will be also recognized by the skilled artisan, polynucleotides may be single-stranded (coding or antisense) or double-stranded, and may be DNA (genomic, cDNA or synthetic) or RNA molecules. RNA molecules may include HnRNA molecules, which contain introns and correspond to a DNA molecule in a one-to-one manner, and mRNA molecules, which do not contain introns. Additional coding or non-coding sequences may, but need not, be present within a polynucleotide according to the present disclosure, and a polynucleotide may, but need not, be linked to other molecules and/or support materials. Polynucleotides may comprise a native sequence or may comprise a sequence that encodes a variant or derivative of such a sequence.

Therefore, according to these and related embodiments, the present disclosure also provides polynucleotides encoding the *Borrelia* spp. T-cell epitope-containing peptides described herein. In certain embodiments, polynucleotides are provided that comprise some or all of a polynucleotide sequence encoding a peptide as described herein and complements of such polynucleotides.

In other related embodiments, polynucleotide variants may have substantial identity to a polynucleotide sequence encoding a *Borrelia* spp. T-cell epitope-containing peptide described herein. For example, a polynucleotide may be a polynucleotide comprising at least 80% sequence identity, preferably at least 85%, 90%, 95%, 96%, 97%, 98%, or 99% or higher, sequence identity compared to a reference polynucleotide sequence such as a sequence encoding a *Borrelia* spp. T-cell epitope-containing peptide described herein (e.g., a peptide having one of SEQ ID NOS:1-33 as its amino acid sequence), using the methods described herein, (e.g., BLAST analysis using standard parameters, as described below). One skilled in this art will recognize that these values can be appropriately adjusted to determine corresponding identity of polypeptides or peptides encoded by two nucleotide sequences by taking into account codon degeneracy, amino acid similarity, reading frame positioning and the like.

In another embodiment, polynucleotides are provided that are capable of hybridizing under moderate to high stringency conditions to a polynucleotide sequence encoding a *Borrelia* spp. T-cell epitope-containing peptide, or variant thereof, provided herein, or a fragment thereof, or a complementary sequence thereof. Hybridization techniques are well known in the art of molecular biology. For purposes of illustration, suitable moderately stringent conditions for testing the hybridization of a polynucleotide as provided herein with other polynucleotides include prewashing in a solution of 5×SSC, 0.5% SDS, 1.0 mM EDTA (pH 8.0); hybridizing at 50° C.–60° C., 5×SSC, overnight; followed by washing twice at 65° C. for 20 minutes with each of 2×, 0.5× and 0.2×SSC containing 0.1% SDS. One skilled in the art will understand that the stringency of hybridization can be readily manipulated, such as by altering the salt content of the hybridization solution and/or the temperature at which the hybridization is performed. For example, in another embodiment, suitable highly stringent hybridization conditions include those described above, with the exception that the temperature of hybridization is increased, e.g., to 60° C.–65° C. or 65° C.–70° C.

As also described elsewhere herein, determination of the three-dimensional structures of representative *Borrelia* spp. T-cell epitope-containing peptides (e.g., SEQ ID NOS:1-33 or variants thereof as provided herein) may be made through routine methodologies such that substitution, addition, deletion or insertion of one or more amino acids with selected natural or non-natural amino acids can be virtually modeled for purposes of determining whether a so derived structural variant retains the space-filling properties of presently disclosed species. A variety of computer programs are known to the skilled artisan for determining appropriate amino acid substitutions (or appropriate polynucleotides encoding the amino acid sequence) within a peptide such that, for example, Borrelia-specific T-cell recognition is maintained.

The polynucleotides described herein, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in an intended recombinant DNA protocol to produce the presently disclosed Borrelia T-cell epitope-containing peptides. For example, illustrative polynucleotide segments with total lengths of about 10,000, about 5000, about 3000, about 2,000, about 1,000, about 500, about 200, about 100, about 50 base pairs in length, and the like, (including all intermediate lengths) are contemplated to be useful.

When comparing polynucleotide sequences, two sequences are said to be "identical" if the sequence of nucleotides in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., *Unified Approach to Alignment and Phylogenes*, pp. 626-645 (1990); *Methods in Enzymology* vol. 183, Academic Press, Inc., San Diego, Calif.; Higgins, D. G. and Sharp, P. M., *CABIOS* 5:151-153 (1989); Myers, E. W. and Muller W., *CABIOS* 4:11-17 (1988); Robinson, E. D., *Comb. Theor* 11:105 (1971); Santou, N. Nes, M., *Mol. Biol. Evol.* 4:406-425 (1987); Sneath, P. H. A. and Sokal, R. R., *Numerical Taxonomy—the Principles and Practice of Numerical Taxonomy*, Freeman Press, San Francisco, Calif. (1973); Wilbur, W. J. and Lipman, D. J., *Proc. Natl. Acad., Sci. USA* 80:726-730 (1983).

Alternatively, optimal alignment of sequences for comparison may be conducted by the local identity algorithm of Smith and Waterman, *Add. APL. Math* 2:482 (1981), by the identity alignment algorithm of Needleman and Wunsch, *J. Mol. Biol.* 48:443 (1970), by the search for similarity methods of Pearson and Lipman, *Proc. Natl. Acad. Sci. USA* 85: 2444 (1988), by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One preferred example of algorithms that are suitable for determining percent sequence identity and sequence similarity are the BLAST and BLAST 2.0 algorithms, which are described in Altschul et al., *Nucl. Acids Res.* 25:3389-3402 (1977), and Altschul et al., *J. Mol. Biol.* 215:403-410 (1990), respectively. BLAST and BLAST 2.0 can be used, for example with the parameters described herein, to determine percent sequence identity among two or more the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff, *Proc. Natl. Acad. Sci. USA* 89:10915 (1989)) alignments, (B) of 50, expectation (E) of 10, M=5, N=−4 and a comparison of both strands.

In certain embodiments, the "percentage of sequence identity" is determined by comparing two optimally aligned sequences over a window of comparison of at least 20 positions, wherein the portion of the polynucleotide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there are many nucleotide sequences that encode a Borrelia spp. T-cell epitope-containing peptide as described herein. Some of these polynucleotides bear minimal sequence identity to the nucleotide sequence of the native or original polynucleotide sequence that encodes Borrelia spp. T-cell epitope-containing peptides described herein. Nonetheless, polynucleotides that vary due to differences in codon usage are expressly contemplated by the present disclosure. In certain embodiments, sequences that have been codon-optimized for mammalian expression are specifically contemplated.

Therefore, in another embodiment of the invention, a mutagenesis approach, such as site-specific mutagenesis, may be employed for the preparation of variants and/or derivatives of the Borrelia T-cell epitope-containing peptides described herein. By this approach, specific modifications in a polypeptide sequence can be made through mutagenesis of the underlying polynucleotides that encode them.

These techniques provides a straightforward approach to prepare and test sequence variants, for example, incorporating one or more of the foregoing considerations, by introducing one or more nucleotide sequence changes into the polynucleotide.

Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Mutations may be employed in a selected polynucleotide sequence to improve, alter, decrease, modify, or otherwise change the properties of the polynucleotide itself, and/or alter the properties, activity, composition, stability, or primary sequence of the encoded polypeptide.

According to certain related embodiments there is provided a recombinant host cell which comprises one or more constructs as described herein; a nucleic acid encoding a Borrelia spp. T-cell epitope-containing peptide or variant thereof; and a method of producing of the encoded product, which method comprises expression from encoding nucleic acid therefor. Expression may conveniently be achieved by culturing under appropriate conditions recombinant host cells containing the nucleic acid. Following production by expression, a Borrelia spp. T-cell epitope-containing peptide may be isolated and/or purified using any suitable technique, and then used as desired.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The recombinant expression of peptides in prokaryotic cells such as E. coli is well established in the art, as also is expression in eukaryotic cells in culture.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g., phage, or phagemid, as appropriate. For further details see, for example, Molecular Cloning: a Laboratory Manual: 4th edition, Green and Sambrook, 2012, Cold Spring Harbor Laboratory Press, Cold Spring Harbor, N.Y. Many known techniques and protocols for manipulation of nucleic acid, for example in preparation of nucleic acid constructs, mutagenesis, sequencing, introduction of DNA into cells and gene expression, and analysis of proteins, are described in detail in Current Protocols in Molecular Biology, Ausubel et al. eds., John Wiley & Sons, N Y, 2015, or subsequent updates thereto.

The term "host cell" is used to refer to a cell into which has been introduced, or which is capable of having introduced into it, a nucleic acid sequence encoding one or more of the herein described Borrelia T-cell epitope-containing peptides, and which further expresses or is capable of expressing a selected gene of interest, such as a gene encoding any herein described Borrelia T-cell epitope-containing peptide. The term includes the progeny of the parent cell, whether or not the progeny are identical in morphology or in genetic make-up to the original parent, so long as the selected gene is present. Accordingly there is also contemplated a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. In one embodiment, the nucleic acid is integrated into the genome (e.g. chromosome) of the host cell. Integration may be promoted by inclusion of sequences which promote recombination with the genome, in accordance-with standard techniques.

The present invention also provides, in certain embodiments, a method which comprises using a construct as stated above in an expression system in order to express a particular polypeptide such as a Borrelia spp. T-cell epitope-containing peptide as described herein. The term "transduction" is used to refer to the transfer of genes from one bacterium to another, usually by a phage. "Transduction" also refers to the acquisition and transfer of eukaryotic cellular sequences by retroviruses. The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, e.g., Green and Sambrook, Molecular Cloning: a Laboratory Manual: 4th edition, 2012, Cold Spring Harbor Laboratory Press, Cold Spring Harbor, N.Y.; Current Protocols in Molecular Biology, Ausubel et al. eds., John Wiley & Sons, N Y, 2015, or subsequent updates thereto. Such techniques can be used to introduce one or more exogenous DNA moieties into suitable host cells.

The term "transformation" as used herein refers to a change in a cell's genetic characteristics, and a cell has been transformed when it has been modified to contain a new DNA. For example, a cell is transformed where it is genetically modified from its native state. Following transfection or transduction, the transforming DNA may recombine with that of the cell by physically integrating into a chromosome of the cell, or may be maintained transiently as an episomal element without being replicated, or may replicate independently as a plasmid. A cell is considered to have been stably transformed when the DNA is replicated with the division of the cell. The term "naturally occurring" or "native" when used in connection with biological materials such as nucleic acid molecules, polypeptides, host cells, and the like, refers to materials which are found in nature and are not manipulated by a human. Similarly, "non-naturally occurring" or "non-native" as used herein refers to a material that is not found in nature or that has been structurally modified or synthesized by a human.

It will be appreciated that the practice of the several embodiments of the present invention will employ, unless indicated specifically to the contrary, conventional methods in virology, immunology, microbiology, molecular biology and recombinant DNA techniques that are within the skill of the art, and many of which are described below for the purpose of illustration. Such techniques are explained fully in the literature. See, e.g., Green and Sambrook, Molecular Cloning: a Laboratory Manual: 4th edition, 2012, Cold Spring Harbor Laboratory Press, Cold Spring Harbor, N.Y.; Current Protocols in Molecular Biology, Ausubel et al. eds., John Wiley & Sons, N Y, 2015; *Current Protocols in Molecular Biology or Current Protocols in Immunology*, John Wiley & Sons, New York, N.Y. (2009); Ausubel et al., *Short Protocols in Molecular Biology*, 3$^{rd}$ ed., Wiley & Sons, 1995; Sambrook and Russell, *Molecular Cloning: A Laboratory Manual* (3rd Edition, 2001); Maniatis et al. *Molecular Cloning: A Laboratory Manual* (1982); *DNA Cloning: A Practical Approach*, vol. I & II (D. Glover, ed.); *Oligonucleotide Synthesis* (N. Gait, ed., 1984); *Nucleic Acid Hybridization* (B. Hames & S. Higgins, eds., 1985); *Transcription and Translation* (B. Hames & S. Higgins, eds., 1984); *Animal Cell Culture* (R. Freshney, ed., 1986); Perbal, *A Practical Guide to Molecular Cloning* (1984) and other like references.

Each embodiment described in this specification is to be applied mutatis mutandis to every other embodiment unless expressly stated otherwise.

Standard techniques may be used for biochemical and immunochemical and immunological assays, recombinant DNA, oligonucleotide synthesis, microbial and mammalian cell and tissue culture and transformation (e.g., electroporation, lipofection). Enzymatic reactions and purification techniques may be performed according to manufacturer's specifications or as commonly accomplished in the art or as described herein. These and related techniques and procedures may be generally performed according to conventional methods well known in the art and as described in various general and more specific references in microbiology, molecular biology, biochemistry, molecular genetics, cell biology, virology and immunology techniques that are cited and discussed throughout the present specification. See, e.g., Sambrook, et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); *Oligonucleotide Synthesis* (N. Gait, Ed., 1984); *Nucleic Acid Hybridization* (B. Hames & S. Higgins, Eds., 1985); *Transcription and Translation* (B. Hames & S. Higgins, Eds., 1984); *Animal Cell Culture* (R. Freshney, Ed., 1986); Perbal, *A Practical Guide to Molecular Cloning* (1984); Next-Generation Genome Sequencing (Janitz, 2008 Wiley-VCH); *PCR Protocols (Methods in Molecular Biology)* (Park, Ed., 3$^{rd}$ Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); Riott, *Essential Immunology*, 6th Edition, (Blackwell Scientific Publications, Oxford, 1988); *Embryonic Stem Cells: Methods and Protocols* (Methods in Molecular Biology) (Kurstad Turksen, Ed., 2002); *Embryonic Stem Cell Protocols: Volume I: Isolation and Characterization* (Methods in Molecular Biology) (Kurstad Turksen, Ed., 2006); *Embryonic Stem Cell Protocols: Volume II: Differentiation Models* (Methods in Molecular Biology) (Kurstad Turksen, Ed., 2006); *Human Embryonic Stem Cell Protocols* (Methods in Molecular Biology) (Kursad Turksen Ed., 2006); *Mesenchymal Stem Cells: Methods and Protocols* (Methods in Molecular Biology) (Darwin J. Prockop, Donald G. Phinney, and Bruce A. Bunnell Eds., 2008); *Hematopoietic Stem Cell Protocols* (Methods in Molecular Medicine) (Christopher A. Klug, and Craig T. Jordan Eds., 2001); *Hematopoietic Stem Cell Protocols* (Methods in Molecular Biology) (Kevin D. Bunting Ed., 2008) *Neural Stem Cells: Methods and Protocols* (Methods in Molecular Biology) (Leslie P. Weiner Ed., 2008).

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well known and commonly used in the art. Standard techniques may be used for recombinant technology, molecular biological, microbiological, chemical syntheses, chemical analyses, pharmaceutical preparation, formulation, and delivery, and treatment of patients.

Unless the context requires otherwise, throughout the present specification and claims, the word "comprise" and variations thereof, such as, "comprises" and "comprising" are to be construed in an open, inclusive sense, that is, as "including, but not limited to". By "consisting of" is meant including, and typically limited to, whatever follows the phrase "consisting of." By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and may or may not be present depending upon whether or not they affect the activity or action of the listed elements.

In this specification and the appended claims, the singular forms "a," "an" and "the" include plural references unless the content clearly dictates otherwise. As used herein, in particular embodiments, the terms "about" or "approximately" when preceding a numerical value indicates the value plus or minus a range of 5%, 6%, 7%, 8% or 9%. In other embodiments, the terms "about" or "approximately" when preceding a numerical value indicates the value plus or minus a range of 10%, 11%, 12%, 13% or 14%. In yet other embodiments, the terms "about" or "approximately" when preceding a numerical value indicates the value plus or minus a range of 15%, 16%, 17%, 18%, 19% or 20%.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

EXAMPLES

Example 1. Lyme Disease Detection and Treatment Efficacy Monitoring by Secondary In Vitro T-Cell Response to Artificial Peptide Composition This example describes evaluating the ability of specific peptides, derived from regions of individual *Borrelia* spp. proteins and contained within a multi-peptide cocktail, to induce interferon-γ production in vitro by activated T-cells obtained from LD patients. In particular, a cocktail comprised of *Borrelia* spp.-specific peptides was tested for its ability to induce interferon-γ release in vitro by Lyme disease-specific activated T-cells in blood samples obtained from patients with very early *B. burgdorferi* infections. Levels of in vitro interferon-γ production were also determined from T-cells collected at a first timepoint from LD patients immediately prior to antibiotic therapy, and again from T-cells collected at a second timepoint that was approximately 60 days after the patients were treated effectively with antibiotics.

Materials and Methods

Selection and Preparation of Lyme Disease-Specific Protein Peptides.

*Borrelia* flagellin (FlaB), decorin binding protein (DbpB), common antigen (p66), and outer surface protein C (OspC) have each been used reliably to detect antibodies produced in response to infection with LD spirochetes.

A cocktail of peptides comprised of *Borrelia*-specific peptide regions selected from within each of these *Borrelia* proteins (Tables 2-3) was evaluated to activate T-cells in peripheral blood samples obtained from LD patients shortly after infection with Lyme spirochetes. To increase the specificity of the peptide composition for potential stimulation of LD-relevant T-cells, the full protein sequences were first analyzed by BLAST algorithm to identify appropriate *Borrelia*-specific regions (Table 4). Synthetic peptides were then synthesized from the specific regions within each protein; each peptide was approximately 15-25 amino acids long with overlapping 10-15 amino terminal ends (Table 3).

Enrollment of Patients.

Patients with suspected early Lyme disease characterized by tick exposure and subsequent development of a skin lesion with characteristics consistent with erythema migrans (EM) were then solicited for participation in a proof-of-concept study. Informed consent was obtained from each volunteer, and each subject had a presumptive diagnosis of Lyme disease that necessitated treatment with 100 mg of doxycycline twice daily for a minimum of 10 days, with the exception of one subject (#6) who was treated for only one day.

TABLE 4

Amino acid sequences of *Borrelia* spp.-specific regions within FlaB, BbpB, p66, and OspC.

FlaB, flagellin, partial [*Borrelia burgdorferi*], GenBank: ACI49679.1
NVRTAEELGM QPAKINTPAS LSGSQASWTL RVHVGANQDE (51-90) [SEQ ID NO: 34]

QDEAIAVNIYAANVANLFSG (88-107) [SEQ ID NO: 35]

SLAKIENAIRMISDQRANL (156-174) [SEQ ID NO: 36]

DbpB (decorin binding protein B), partial [*Borrelia burgdorferi*],
GenBank: AAC70029.1
SIVMVLFFDL LVACSIGLVE RTNAALESSS KDLKNKILKI KKEATGKGVL FEAFTGLKTG
SKVTSGGLAL REAKVQAIVE TGKFLKIIEE EALKLKETGN SGQFLAMFDL MLEVVESLED
VGIIGLKARV LEESKNNPIN TAERLLAAKA QIENQLKVVK EKQNIENGGE KKNNKSKKKK
(1-180) [SEQ ID NO: 37]

p66, Integral outer membrane protein p66 [*Borrelia burgdorferi* B31],
GenBank: AAC66949.1
FGLSGAYGNE TFNNSSITYS LKDKSVVGND LLSPTLSNSA ILASFGAKYK LGLTKINDKN
TYLILQMGTD FGIDPFASDF SIFGHISKAA NFKKETPSDP NKKAEIFDPN GNALNFSKNT
ELGIAFSTGA SIGFAWNKDT GEKESWAIKG (251-400) [SEQ ID NO: 38]

OspC, outer surface protein C [*Borrelia burgdorferi*], GenBank: ABQ42983.1
ATKAIGKKIQQNGGLAVEAGH (55-75) [SEQ ID NO: 39]

KEMLANSVKELTSPI (171-185) [SEQ ID NO: 40]

are abundantly expressed on the surface of *Borrelia* spp. at different times during mammalian infection. Specifically, FlaB is a major filament protein of flagella that is prominently expressed during late disseminated and early local stages of infection. DbpB is an adhesin that is upregulated during tick feeding and/or shortly after transmission and appears during the early disseminated stage of infection, and p66 is an integrin binding protein that fosters bacterial attachment to immune cells and is expressed after dissemination of the infection. Additionally, expression of OspC appears during the early local stage and is believed to be essential for establishing mammalian infection, and OspC-specific antibodies are the predominant antibody during early human LD. *Borrelia* spp. FlaB, DbpB, p66 and OspC Collection and Processing of Blood Samples.

During the pre-treatment (initial presentation) and 60 day post-treatment visits, blood samples were collected in green-top (lithium-heparin) tubes and processed promptly. The blood in one tube was centrifuged to separate the plasma, and the separated plasma was removed and stored at −80° C. until tested. A separate one-ml volume of blood was also transferred immediately to a sterile pyrogen-free tube (Cellestis Ltd, Carnegie, Victoria, Australia) that was pre-loaded with a 10-μl volume of the pool of 33 *Borrelia* peptides [SEQ ID NOS:1-33] shown in Table 3 (1 μg of each peptide). In addition, separate one-ml volumes of blood were added to separate tubes that did not contain peptide (nil) or were pre-loaded with a mitogen control. The contents in each tube were then mixed thoroughly and incubated at 37° C. for 18-24 hours.

Detection of Interferon-γ.

After incubation, the blood plasma was harvested after centrifugation at 3000×g for 15 min to remove cells, and the level of interferon-γ in the plasma was immunochemically quantitated using the QuantiFERON®-TB Gold ELISA kit (Cellestis Ltd) as instructed by the manufacturer. The QuantiFERON® assay is established for testing blood samples from tuberculosis (TB) patients to confirm infection with *Mycobacterium tuberculosis* by detecting IFN-γ produced by secondary in vitro activated T-cells obtained after the T-cells have been stimulated by exposure to specific *Mycobacterium* spp. peptides. Here, the QuantiFERON® platform was adapted to also detect IFN-γ produced by T-cells activated in response to infection with *B. burgdorferi* instead of *M. tuberculosis*. Prior to evaluating the plasma samples, a significant reactivity cut-off value was first determined by testing sera from eight volunteer subjects having no previous history or suspicion of Lyme disease. Blood was collected by venipuncture in clot-activator tubes, and the serum was removed and tested immediately. The mean of the resultant values was then calculated and OD values ≥2 standard deviations above the mean value (≥0.452) were considered significant ("[a]").

Serodiagnostic Confirmation of LD.

Paired (pre- and post-treatment from the same subject) plasma samples were also tested for anti-C6 antibodies and Western blot reactivity. Anti-C6 antibodies were detected by ELISA as described previously (Jobe et al., 2008. Significantly improved accuracy of diagnosis of early Lyme disease by peptide enzyme-linked immunosorbent assay based on the borreliacidal antibody epitope of *Borrelia burgdorferi* OspC. C/in Vacc Immunol 15:981-985). Prior to the evaluation, significant reactivity cut-off values were determined by testing 15 well-characterized sera from volunteer subjects with no previous history or suspicion of LD. Blood was collected by venipuncture in clot-activator tubes, and the serum was removed and tested immediately. The mean of the resultant optical density (OD) values was then calculated and OD values ≥2 standard deviations above the mean (IgM≥0.534, IgG≥0.140) were considered significant ("[a]"). An appropriate positive control and normal control serum were also included in separate wells on the ELISA plate.

Western immunoblot reactivity of serum immunoglobulins toward electrophoretically separated *Borrelia* antigens (Mogilyanski et al., 2004 *Clin Diag Lab Immunol* 11:924) was detected using a commercially-available kit (Marblot™, Trinity Biotech, Bray, Co Wicklow, Ireland) according to the manufacturer's recommendations. The criteria recommended by the Centers for Disease Control (CDC, Atlanta, Ga., USA) were used to determine positivity (IgM—at least two of 23, 39, or 41 bands detected, IgG—at least five of 18, 23, 28, 30, 39, 41, 45, 58, 66, or 93 bands detected).

Results

Study Cohort.

A total of 21 patients (18 years of age or older) completed the study. Each was exposed to questing *Ixodes scapularis* ticks or had documented tick bites within the 30 days prior to detecting presumed single or multiple erythema migrans lesion(s), and, with the exception of subject #6 who received antibiotic therapy (doxycycline) for only one day, each subject was treated with doxycycline for at least 10 days, which is a treatment regimen that nearly universally results in successful elimination of the spirochetes during early stages of the illness (Kowalski et al., 2010 *Clin Infect Dis* 50:512-520). As further support of effective therapy, each subject was interviewed at the time of providing a convalescent blood sample, and no individuals complained of ongoing abnormalities.

Serodiagnostic Confirmation of LD.

Acute and convalescent sera from each subject were initially evaluated for anti-C6 antibodies or Western blot reactivity to obtain serodiagnostic confirmation that each enrollee was infected with *B. burgdorferi*. The acute sera from 10 (48%) subjects contained significant levels of IgM anti-C6 antibodies and two (10%) additional subjects seroconverted during convalescence (Table 5). In addition, the acute sera from 12 (57%) subjects contained IgG anti-C6 antibodies, and eight patients producing IgG antibodies were producing IgM antibodies. Moreover, significant levels of IgG antibodies were detected in the convalescent sera from four (19%) additional subjects. The collective findings provided serodiagnostic confirmation of Lyme disease in 17 (81%) of the 21 enrollees.

In contrast, acute sera from only two (10%) subjects yielded sufficient IgM antibody reactivities to satisfy the Centers for Disease Control (CDC) criteria for confirmation of *B. burgdorferi* infection (Table 6). In addition, the response increased (more reactive IgM and IgG bands) to confirmatory levels in only four additional subjects after 60 days. Western blotting provided serodiagnostic confirmation in only six (29%) of the 21 enrollees. In addition, subjects that failed to develop anti-C6 antibodies were also negative by Western blot. The combined results from the C6 test and Western blotting failed to provide serodiagnostic confirmation of LD in four (19%) study subjects. More significantly, the levels of antibodies detected by each test procedure had often increased in the convalescent, post-treatment sera, even though the LD spirochetes were almost certainly eliminated by the antibiotic therapy. Therefore, the C6 test or Western blotting could not be relied upon to provide accurate prediction of successful treatment.

TABLE 5

Serodiagnostic confirmation of early Lyme disease by detection of anti-C6 antibodies.

| Subject | Significant anti-C6 antibodies[a] (+/−) | | | |
|---|---|---|---|---|
| | IgM | | IgG | |
| Convalescent | Acute | Convalescent | | Acute |
| 1 | +(0.618) | −(0.512) | +(0.196) | +(0.441) |
| 2 | −(0.125) | −(0.264) | +(0.175) | +(0.761) |
| 3 | +(2.372) | +(0.841) | +(2.804) | +(2.656) |
| 4 | +(0.839) | +(0.991) | +(1.329) | +(1.719) |
| 5 | −(0.245) | −(0.174) | −(0.028) | −(0.124) |
| 6 | −(0.396) | −0.438) | +(0.226) | −(0.071) |
| 7 | +(0.818) | +(1.406) | −(0.036) | +(1.734) |
| 8 | +(0.544) | +(0.678) | +(1.050) | +(2.210) |
| 9 | +(1.980) | +(0.718) | +(2.922) | +(2.540) |
| 10 | −(0.532) | −(0.220) | −(0.074) | +(0.801) |
| 11 | −(0.505) | +(0.698) | −(0.081) | +(1.047) |
| 12 | +(0.534) | −(0.482) | −(0.065) | +(0.249) |
| 13 | −(0.236) | −(0.204) | +(0.198) | −(0.133) |
| 14 | +(0.599) | +(0.309) | +(0.863) | +(0.172) |
| 15 | −(.0209) | −(0.367) | −(0.067) | −(0.236) |
| 16 | +(0.687) | +(1.294) | +(0.561) | +(0.832) |
| 17 | +(1.883) | +(1.273) | +(3.399) | +(3.872) |
| 18 | −(0.308) | +(0.372) | +(3.212) | +(3.226) |
| 19 | −(0.302) | −(0.263) | −(0.000) | −(0.037) |
| 20 | −(0.106) | −(0.143) | −(0.048) | −(0.052) |
| 21 | −(0.277) | −(0.272) | −(0.012) | −(0.042) |

TABLE 6

Serodiagnostic confirmation of early Lyme disease by Western blotting.

| Subject Conva- | Significant Western blot reactivity[a] (+/−) | | | |
|---|---|---|---|---|
| | IgM | | IgG | |
| lescent | Acute | Convalescent | Acute | Convalescent |
| 1 | − | − | − | −(41) |
| 2 | − | − | − | −(41) |
| 3 | −(41) | −(41) | −(41) | −(41) |
| 4 | −(41) | − | −(39, 41, 45) | −(39, 41) |
| 5 | − | − | − | −(41) |
| 6 | − | − | − | − |
| 7 | −(23) | −(23) | −(41) | −(23, 39, 41, 45) |
| 8 | − | − | −(41) | −(41, 58) |
| 9 | +(23, 41) | +(23, 41) | −(23, 41, 45) | −(23, 41, 45) |
| 10 | −(23) | +(23, 39, 41) | −(23, 41) | −(23, 39, 41) |
| 11 | − | −(23) | − | −(23, 39, 41) |
| 12 | −(23) | +(23, 41) | − | − |
| 13 | − | − | −(41) | −(41) |
| 14 | − | − | − | − |
| 15 | − | −(23) | − | −(23, 41) |
| 16 | −(23) | +(23, 41) | − | −(23, 41) |
| 17 | +(23, 39, 41) | +(23, 39, 41) | −(23, 39, 41) | −(23, 39, 41, 45) |
| 18 | −(23) | −(23) | −(41, 45, 58) | +(18, 41, 45, 58, 66) |
| 19 | −(23) | −(23) | − | − |
| 20 | − | − | −(41) | −(41) |
| 21 | − | − | − | − |

Detection of Interferon-γ after Stimulation of T-Cells by the *Borrelia* Peptide Pool.

Interferon-γ levels were determined by immunodetection of released IFN-γ following in vitro stimulation, using the pool of 33 *Borrelia* peptides shown in Table 2, of the peripheral blood T-cells that were collected during the acute and convalescent stages of the illness from the 17 subjects confirmed by serodiagnosis (supra) to have contracted LD. Significant levels of interferon-γ were detected (Table 7, Acute, "+") in test incubation mixtures from the 10 (59%) subjects (Table 5) from whom acute sera had been obtained, as determined by antibody testing. Additionally, the interferon-γ response was not detected in any additional subjects after convalescence (Table 7, Convalescent) and, in contrast to the findings for the C6 and Western immunoblot tests for antibodies in the samples, the levels of interferon-γ in the initial 10 positive patients either decreased appreciably (n=4, Table 7, Convalescent, "+") or the IFN-γ response was no longer detectable (n=6).

The possibility was then explored as to whether detectably activated (on the basis of IFN-γ release in response to the *Borrelia* peptide pool) T-cells were absent from blood sample collected following antibiotic therapy, coincident with elimination of the spirochetes after such treatment for LD. To address this question, the mean interferon-γ reactivities that were detected immediately prior to antibiotic therapy (see FIG. 1, "IFN-γ before") were compared to the mean interferon-γ reactivities that were detected post-treatment (see FIG. 1, "IFN-γ after"). It was observed that the mean reactivity decreased significantly (p value=0.0002), coincident with the administration of treatment and with the clinical resolution of symptoms. These findings provided strong evidence that quantitation of interferon-γ production by T-cells in a secondary in vitro response to the herein disclosed *Borrelia* peptide pool was useful to confirm LD during early stages of the illness. Additionally, the activated T-cells decreased rapidly coincident with the successful elimination of the spirochetes by antibiotic therapy, as evidenced by the decreased level of detectable IFN-γ in test incubation mixtures generated in vitro by T-cells collected following antibiotic therapy, in response to the herein described *Borrelia* peptide pool.

TABLE 7

Detection of IFN-γ in confirmed LD patients after activation of T-cells by the peptide pool.

| | Significant[a] IFN-γ (+/−) | |
|---|---|---|
| Subject | Acute | Convalescent |
| 1 | +(1.164) | −(0) |
| 2 | −(0) | −(0.064) |
| 3 | +(5.031) | −(0) |
| 4 | −(0) | −(0) |
| 6 | +(3.860) | +(2.611) |
| 7 | +(1.815) | −(0.159) |
| 8 | −(0.447) | −(0.019) |
| 9 | +(1.689) | +(1.590) |
| 10 | +(0.784) | +(0.460) |
| 11 | +(0.493) | −(0.116) |
| 12 | −(0.291) | −(0) |
| 13 | −(0.329) | −(0) |
| 14 | −(0) | −(0) |
| 15 | +(2.578) | −(0) |
| 16 | +(2.016) | −(0.105) |
| 17 | −(0) | −(0) |
| 18 | +(10.609) | +(1.12) |

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/233,192, filed Sep. 25, 2015 are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for detecting Lyme disease in a subject, or for monitoring efficacy of a treatment for Lyme disease in a subject, comprising: (A) contacting in vitro (i) a first biological sample obtained at a first timepoint a subject known to have or suspected of being at risk for having Lyme disease, wherein the biological sample comprises T-cells and antigen-presenting cells, and (ii) a peptide composition for diagnosis or prognosis of Lyme disease, to obtain a first test incubation mixture; (B) incubating the first test incubation mixture under conditions and for a time sufficient for specific recognition by said T-cells of a *Borrelia* T-cell epitope that is present in said peptide composition to stimulate generation of a T-cell immune response indicator; and (C) detecting a first level of the T-cell immune response indicator in the first test incubation mixture, wherein presence of a *Borrelia* infection in the subject is indicated by detection in (C) of said first level of the T-cell immune response indicator that is increased relative to a first control level of the T-cell immune response indicator obtained by incubating the first biological sample in a first control incubation without the peptide composition for diagnosis or prognosis of Lyme disease, and wherein the peptide composition for diagnosis or prognosis of Lyme disease comprises:

(a) 1, 2, 3, 4, or 5 isolated FlaB peptides that are each not more than 50 amino acids in length and that each comprise a *Borrelia* T-cell epitope and are selected from the FlaB peptides having the amino acid sequences set forth in SEQ ID NOS: 1 or 3; or one or more variants thereof having at least 80% amino acid sequence identity to the amino acid sequences set forth in SEQ ID NOS: 1 or 3;

(b) 1, 2, 3, 4, 5, 6, 7, 8, 9, 10, 11, 12, or 13 isolated DbpB peptides that each comprise a *Borrelia* T-cell epitope and are selected from (i) DbpB peptides of not more than 50 amino acids in length, the DbpB peptides having the amino acid sequences set forth in SEQ ID NOS: 11 or 16, or one or more variants thereof having at least 80% amino acid sequence identity to the amino acid sequences set forth in SEQ ID NOS:11 or 16, and (ii) DbpB peptides of 20, 21, 22, 23, or 24 amino acids in length, the DbpB peptides having the amino acid sequence set forth in SEQ ID NO:6, or one or more variants thereof having at least 80% amino acid sequence identity to the amino acid sequence set forth in SEQ ID NO:6;

(c) 1, 2, 3, 4, 5, 6, 7, 8, 9, 10, 11, 12, or 13 isolated p66 peptides that are each not more than 50 amino acids in length and that each comprise a *Borrelia* T-cell epitope and are selected from the p66 peptides having the amino acid sequences set forth in SEQ ID NOS: 19, 25, or 30, or one or more variants thereof having at least 80% amino acid sequence identity to the amino acid sequences set forth in SEQ ID NOS: 19, 25, or 30; and (d) 1 or 2 isolated OspC peptides that each comprise a *Borrelia* T-cell epitope and are selected from (i) OspC peptides of 21, 22, 23, 24, 25, 26, 27, 28, 29, 30, 31, 32, 33, 34, 35, 36, 37, 38, 39, 40, 41, 42, 43, 44, 45, or 46 amino acids in length, the OspC peptides having the amino acid sequence set forth in SEQ ID NO:32, or one or more variants thereof having at least 80% amino acid sequence identity to the amino acid sequences set forth in SEQ ID NOS:32, and (ii) OspC peptides of not more than 50 amino acids in length, the OspC peptides having the amino acid sequence set forth in SEQ ID NO:33, or one or more variants thereof having at least 80% amino acid sequence identity to the amino acid sequence set forth in SEQ ID NO:33;

and thereby detecting Lyme disease in the subject, or monitoring efficacy of the treatment for Lyme disease in the subject.

2. The method of claim 1 wherein the first timepoint is prior to administration to the subject of treatment for Lyme disease.

3. The method of claim 1 wherein Lyme disease comprises an infection with at least one pathogenic *Borrelia* species.

4. The method of claim 3 wherein the pathogenic *Borrelia* species is pathogenic in humans.

5. The method of claim 4 wherein the *Borrelia* species that is pathogenic in humans is selected from *Borrelia burgdorferi*, *Borrelia burgdorferi* sensu stricto, *Borrelia azfelii*, *Borrelia garinii*, *Borrelia valaisiana*, *Borrelia spielmanii*, *Borrelia bissettii*, *Borrelia lusitaniae*, and *Borrelia bavariensis*.

6. The method of claim 1 wherein the treatment for Lyme disease comprises administering an antibiotic to the subject.

7. The method of claim 6 wherein the antibiotic is selected from tetracyclines; oxytetracycline, tetracycline, doxycycline, or minocycline; penicillins; amoxicillin or penicillin; cephalosporins; cefaclor, cefbuperazone, cefminox, cefotaxime, cefotetan, cefmetazole, cefoxitin, cefuroxime axetil, cefuroxime acetyl, ceftin, or ceftriaxone; macrolides; azithromycin, clarithromycin, or erythromycin.

8. The method of claim 1 wherein the biological sample comprises at least one of (a) whole blood, (b) a cellular fraction of whole blood, (c) isolated peripheral blood white cells, (d) isolated peripheral blood mononuclear cells, (e) cerebrospinal fluid, or (f) synovial fluid.

9. The method of claim 1 wherein the T-cell immune response indicator is interferon-gamma (IFN-γ).

10. The method of claim 9 wherein the IFN-γ is soluble IFN-γ released by the T-cells.

11. The method of claim 1 wherein the T-cell immune response indicator comprises at least one of T-cell proliferation and expression of a T-cell cytokine.

12. The method of claim 11 wherein the T-cell cytokine is selected from IL-1α, IL-1β, IL-2, IL-10, IL-12, IL-17, TNF-α, TNF-β, and IFN-γ.

13. The method of claim 11 wherein expression of the T-cell cytokine is detected as soluble T-cell cytokine released by the T-cells.

14. The method of claim 13 wherein the T-cell cytokine is selected from IL-1α, IL-1β, IL-2, IL-10, IL-12, IL-17, TNF-α, TNF-β, and IFN-γ.

15. The method of claim 14 wherein the T-cell cytokine is detected by determining detectable specific binding of a binding agent to the T-cell cytokine.

16. The method of claim 15 wherein the binding agent comprises at least one antibody that binds specifically to the T-cell cytokine.

17. The method of claim 16 wherein the at least one antibody is selected from a monoclonal antibody and a polyclonal antibody.

18. The method of claim 16 wherein the at least one antibody is immobilized on a solid phase.

* * * * *